United States Patent
Cao et al.

(10) Patent No.: US 10,359,375 B2
(45) Date of Patent: Jul. 23, 2019

(54) PHOTON COUNT-BASED RADIATION IMAGING SYSTEM, METHOD AND DEVICE THEREOF

(71) Applicant: NANOVISION TECHNOLOGY (BEIJING) CO., LTD., Beijing (CN)

(72) Inventors: Hongguang Cao, Beijing (CN); Yunxiang Li, Beijing (CN); Hailiang Zheng, Beijing (CN)

(73) Assignee: NANOVISION TECHNOLOGY (BEIJING) CO., LTD., Beijing (CN)

( * ) Notice: Subject to any disclaimer, the term of this patent is extended or adjusted under 35 U.S.C. 154(b) by 463 days.

(21) Appl. No.: 15/031,657

(22) PCT Filed: Oct. 23, 2014

(86) PCT No.: PCT/CN2014/089368
§ 371 (c)(1),
(2) Date: Apr. 22, 2016

(87) PCT Pub. No.: WO2015/058702
PCT Pub. Date: Apr. 30, 2015

(65) Prior Publication Data
US 2016/0266054 A1    Sep. 15, 2016

(30) Foreign Application Priority Data

Oct. 23, 2013 (CN) .......................... 2013 1 0504035
Apr. 4, 2014 (CN) .......................... 2014 1 0137171
(Continued)

(51) Int. Cl.
*G01N 23/00* (2006.01)
*G01N 23/083* (2018.01)
(Continued)

(52) U.S. Cl.
CPC ........... *G01N 23/083* (2013.01); *A61B 6/032* (2013.01); *A61B 6/4241* (2013.01); *A61B 6/484* (2013.01);
(Continued)

(58) Field of Classification Search
CPC ......... G01T 1/247; G01T 1/36; G01N 23/087; G01N 2223/419; G01N 2223/501;
(Continued)

(56) References Cited

U.S. PATENT DOCUMENTS 7,187,756 B2    3/2007  Gohno
7,606,346 B2    10/2009 Tkaczyk et al.
(Continued)

FOREIGN PATENT DOCUMENTS

CN    1589744    3/2005
CN    1725000    1/2006
(Continued)

OTHER PUBLICATIONS

Yu Ai-min;Li Zheng;Zhang Di, Research of phase retrieval method for micro-focus X-ray phase contrast imaging,Nuclear Electronics 8L Detection Tech, Nov. 2006, p. 883-885, vol. 26 No. 6, Nuclear Electronics 8L Detection Tech, Beijing China.
(Continued)

*Primary Examiner* — Dani Fox
(74) *Attorney, Agent, or Firm* — Kirton McConkie; Evan R. Witt

(57) ABSTRACT

A photon count-based radiation imaging system. The invention also relates to a method of implementing X-ray imaging in said system, and to key apparatus of said system. In the system, an x-ray source directs x-rays at a sample on a scanning platform. When the x-rays pass through said sample, photons carrying information about characteristics of the material at various spatial positions are produced. A
(Continued)

photon count detector counts the photons on an imaging plane, obtains incident photon projection data and energy data, and transmits same to a 3D reconstruction system. The 3D reconstruction system reconstructs, on the basis of said projection data and energy data, the 3D structure and the matter composition inside the sample, then performs digital dyeing on the component parts of the sample, thereby differentiating the matter composition of the sample.

9 Claims, 21 Drawing Sheets

(30) Foreign Application Priority Data

Jul. 15, 2014 (CN) .......................... 2014 1 0337142
Oct. 23, 2014 (CN) .......................... 2014 1 0568482

(51) Int. Cl.
*G01T 1/36* (2006.01)
*G01T 1/24* (2006.01)
*G01N 23/087* (2018.01)
*A61B 6/00* (2006.01)
*A61B 6/03* (2006.01)
*G01N 23/046* (2018.01)
*G21K 1/02* (2006.01)
*G21K 1/06* (2006.01)
*H01J 35/08* (2006.01)
*H01J 35/14* (2006.01)

(52) U.S. Cl.
CPC ............ *A61B 6/502* (2013.01); *G01N 23/046* (2013.01); *G01N 23/087* (2013.01); *G01T 1/24* (2013.01); *G01T 1/247* (2013.01); *G01T 1/36* (2013.01); *G21K 1/02* (2013.01); *G21K 1/025* (2013.01); *G21K 1/06* (2013.01); *H01J 35/08* (2013.01); *H01J 35/14* (2013.01); *A61B 6/03* (2013.01); *A61B 6/52* (2013.01); *G01N 2223/419* (2013.01); *G01N 2223/501* (2013.01); *G21K 2207/005* (2013.01); *H01J 2235/087* (2013.01)

(58) Field of Classification Search
CPC ...... G01N 23/046; G01N 23/083; A61B 6/03; A61B 6/032; A61B 6/4241
See application file for complete search history.

(56) References Cited

U.S. PATENT DOCUMENTS

| 8,674,313 | B2 | 3/2014 | Cao |
| 9,134,259 | B2 | 9/2015 | Huang |
| 2006/0008046 | A1 | 1/2006 | Ruhrnschopf |
| 2010/0329425 | A1* | 12/2010 | Guo ........................ G01T 1/247 378/91 |
| 2012/0181439 | A1* | 7/2012 | Cao ........................ G01T 1/2018 250/366 |

FOREIGN PATENT DOCUMENTS

| CN | 101214154 | 7/2008 |
| CN | 101532969 | 9/2009 |
| CN | 102099704 | 6/2011 |
| CN | 102221565 | 10/2011 |
| CN | 202522706 | 11/2012 |

OTHER PUBLICATIONS

Andrei V. Bronnikov, Phase-contrast CT: Fundamental theorem and fast image reconstruction algorithms, www.bronnikov-algorithms. com, Aug. 13, 2006, Conference vol. 6318, California USA.

Liu Yijin, X-Ray Phase Contrast Imaging and CT technology, A dissertation submitted for the degree of doctor of philosophy, Apr. 2009, All, University of Science and Technology of China, Hefei, Anhui China.

Mai Zhenhong, Synchrotron radiation light source and application thereof, title of the item is the same with the article ISBN: 9787030365347, Mar. 2013, pp. 658-660 and pp. 663-679, Science Press, Beijing China.

* cited by examiner

Dyed voxel matrix
(digital wax block)

PHOTON COUNT-BASED RADIATION IMAGING SYSTEM, METHOD AND DEVICE THEREOF

BACKGROUND

Technical Field

The present invention relates to a radiation imaging system, particularly to a photon count-based X-ray imaging system, and also to a method for achieving X-ray imaging by the system and key devices thereof, which belong to the field of medical image technologies.

Related Art

The penetrating power of X-rays is particularly strong. When the X-rays pass through a sample made up of light elements such as carbon, hydrogen and oxygen, they leave no observable traces like visible light penetrates glass. This is very adverse for medical diagnosis. For example, for the diagnosis of breast tumor, the breast tumor, in the early stage of the development, is still the focus composed of light elements, the absorption-contrast imaging is helpless, and it is visible to the absorption-contrast imaging until calcification is generated in the late stage of the development of the breast tumor. This has missed the best time to treatment, seriously affecting the patients' chances of recovery.

With continuous development of the X-ray imaging technology, it is found that phase information carried by the X-rays after penetrating the sample can also be used for imaging the internal structure of the sample, and the phase drift section of the X-rays is 100-1000 times higher than the absorption section; the internal structure of the sample can be observed by acquiring phase information and carrying out recovery. For weak absorption materials composed of light elements, the change of the phase of the X-rays is more evident that the change of light intensity. X-ray phase-contrast imaging can more easily detect the internal structure of the sample than the traditional absorption-contrast imaging.

After more than 30 years of development, the X-ray phase-contrast imaging technology mainly uses the following four methods:

(1) Crystal interference contrast-imaging method: A complete crystal is cut into three very thin 3L shapes with bases connected together, which are respectively a beam splitter, a projection crystal and an analysis crystal. An X-ray is incident and passes through the first crystal, and then is diffracted and separated into two beams of coherent light. One beam of light is used as reference light, and a phase changer is placed on a propagation path thereof to continuously change light. The method is relatively strict in demanding mechanical stability of the experiment device; as a final diffraction pattern is detected after the incident X-ray penetrates 3 layers of crystals, the photon utilization is low, and a strong light source or a longer exposure time is required to make up. As the crystal size is limited, the method is only suitable for some small-size samples, and is only applicable to synchronous radiation at present.

(2) Crystal diffraction enhancement method: after heterogeneous X-rays emitted by the X-ray source go through a complete crystal, X-rays of which the incident angle meets the bragg diffraction condition (that is, the condition of producing coherent light interference) can pass through a monochromatic crystal, thus forming monochromatic light. An analysis crystal is placed behind the sample to serve as an angle analyzer, followed by a detector to record images. After the monochromatic light penetrates the sample, the analysis crystal converts phase information to light intensity information. By using the analysis crystal and adjusting the angle of the analysis crystal, X-rays transmitted, refracted and small-angle scattered after passing through the sample are enhanced or weakened, and thus diffraction enhancement imaging has three mechanisms of producing contrast, which are respectively absorption contrast, refraction contrast and extinction contrast obtained by filtering small-angle scattering.

(3) Grating shearing method: the monochromatic light is used to irradiate a grating, and a periodic image may appear at a certain distance behind the grating, that is, the "Tablot-Lau effect", as shown in FIG. 1. By use of the grating self-imaging effect and through design of a light path, an image of a first phase grating is matched with a second absorption grating, then moire fringes formed by the sample are analyzed, and wave fronts can be quantitatively recovered. At present, there are two implementation schemes for the method, one is producing a phase shift of $\pi/2$ and the other is producing a phase shift of $\pi$. The advantage of the method lies in no longer relying on synchrotron radiation light sources with high brightness and higher coherence, thus having an extensive application prospect.

The method (2) and the method (3) are X-ray phase-contrast imaging methods based on optical analysis elements. The function of such optical analysis elements is to generate phase differential images, thus improving the boundary contrast of the images, and quantitative phase recovery needs to be carried out through a certain experimental mechanism and a corresponding algorithm.

(4) Phase-contrast imaging method based on X-ray free propagation: the method is also referred to as an X-ray in-line phase-contrast imaging method, which, according to different light sources used, is divided into monochromatic X-ray in-line phase-contrast imaging and polychromatic X-ray in-line phase-contrast imaging. The polychromatic X-ray in-line is based on a light intensity propagation equation proposed by K. A. Nugent in the University of Melbourne Australia. The in-line method is simpler in implementation, as long as the focal point of the X-ray source is small enough, phase-contrast imaging can be achieved on a device based on absorption contrast, however, as a phase second derivative is obtained with the in-line method, it is relatively difficult in phase recovery.

For example, in a Chinese invention patent application with Application Number of 200410053014.6, an X-ray contrast imaging method and system are disclosed. According to the scheme, the sample is imaged on a detector through in-line outline imaging, a distance between a light source point generated by a microfocus X-ray source and a sample on a scanning stage is adjusted according to the sample, and a distance between the sample and the detector is adjusted at the same time. However, an image obtained according to the scheme is a phase second-order differential image of the sample, how phase recovery is carried out to get a phase map of the sample on the basis of the second-order differential image is not described, nor how slice reconstruction and 3D imaging of phase contrast are achieved is described. In addition, as the brightness of the microfocus X-ray source is very low, the detector takes a longer time to expose, and it is difficult to meet the actual needs of clinical applications.

For another example, in a Chinese invention patent application with Application Number of 200810166472.9, an X-ray grating phase-contrast imaging system and method are disclosed. According to the method, phase-contrast imaging under incoherent conditions of approximate decimeter order-of-magnitude field can be achieved by using an X-light machine, a multi-seam collimator such as a source grating, and two absorption gratings. However, in the technical solution, the making of the grating is still a bottleneck, which will restrict actual application of the grating phase-contrast imaging technology in medicine and industry.

In addition, the existing phase-contrast imaging systems mostly employ a detector based on energy integral, such that the radiation imaging system utilizes the X-rays penetrating the sample at a lower rate. On the other hand, although structural information inside the sample can be obtained by using the detector based on energy integral, the capability of acquiring matter composition information of the sample is insufficient.

In addition, a synchronous radiation X-ray source belongs to a large scientific device, the equipment and maintenance costs are expensive, using it as medical clinical diagnostic equipment is not in line with the principle of effective utilization of energy and resources, and the imaging diagnosis cost cannot be afforded by general patients.

SUMMARY

With respect to the shortcomings of the prior art, a primary technical problem to be solved in the present invention is to provide a photon count detector.

Another technical problem to be solved in the present invention is to provide a photon count-based radiation imaging system.

A further technical problem to be solved in the present invention is to provide a photon count-based radiation imaging method.

To achieve the foregoing invention objectives, the present invention adopts the following technical solutions:

A photon count detector, the photon count detector being a plane-array detector made up of multiple pixel units, wherein each of the pixel units includes a photoelectric conversion layer, a pre-amplifier, an event detection unit, a level discrimination comparator, a pulse shaper, a counter, an accumulator and an output bus;

wherein the photoelectric conversion layer converts a single photon to an electrical signal, and the electrical signal is transmitted to the pre-amplifier for amplification; the event detection unit filters noise in the electrical signal and sends the electrical signal to the level discrimination comparator; the level discrimination comparator grades effective signals which enter the pulse shaper for pulse shaping; and the counter counts pulse signals which are input to the accumulator and output to the bus.

A photon count detector, including a photon count module, a detector core module, a control module and a substrate, wherein the detector core module on the top layer is connected with the photon count module on the second layer; an interface of the photon count module is led out to the back of the photon count module and connected to the control module on the third layer; and the control module leads the interface out to the back of the control module through a silicon via, and is connected to the substrate through tin-lead solder ball flip-chip.

A photon count-based radiation imaging system, including:

an X-ray source, a scanning platform for bearing a sample, a photon count detector and a three-dimensional reconstruction system;

wherein the X-ray source emits X-rays to the sample on the scanning platform, when the X-rays penetrate the sample, photons carrying material feature information in spatial positions are generated, and the photon count detector counts photons on an imaging plane, obtains projection data and energy data of incident photons, and transmits the projection data and the energy data to the three-dimensional reconstruction system; and the three-dimensional reconstruction system reconstructs three-dimensional structures and matter composition classes inside the sample according to the projection data and the energy data, and digitally dyes components of the sample, to identify matter composition of the sample.

A photon count-based radiation imaging method, including:

(1) the X-ray source emitting X-rays to the sample on the scanning platform, and, when the X-rays penetrate the sample, generating photons carrying material feature information in spatial positions;

(2) the photon count detector counting photons on an imaging plane, obtaining projection data and energy data of incident photons, and transmitting the photons to the three-dimensional reconstruction system; and (3) the three-dimensional reconstruction system reconstructing a three-dimensional structure and a matter composition class inside the sample according to the projection data and the energy data, and digitally dying components of the sample, to identify matter composition of the sample.

A photon count-based radiation imaging system, including:

an X-ray source used for generating X-rays, a light source grating used for dividing the X-rays emitted by the X-ray source into multiple coherent light sources;

a sample scanning platform used for bearing a sample under test, a phase grating used for beam-splitting the X-rays and making the beam-split X-rays produce incoherent interference, an analysis grating used for converting phase information of the X-rays to light intensity information of the X-rays, a three-dimensional reconstruction system that three-dimensionally reconstructs structure of the sample according to projection images, and a photon count detector used for making statistics on the number of photons of the X-rays that reach a surface thereof within a certain time period, which form projection images and are transmitted to the three-dimensional reconstruction system;

wherein the light source grating is disposed between the X-ray source and the sample, the phase grating is disposed between the other side of the sample and the analysis grating, the other side of the analysis grating is provided with the photo counting detector, and the photo counting detector is connected with the three-dimensional reconstruction system.

A photon count-based radiation imaging method, including:

step 1: when there is no sample on the sample scanning platform, the radiation imaging system collecting a reference projection image;

step 2: placing a sample on the sample scanning platform, and the radiation imaging system collecting a first projection image;

step 3: rotating the sample scanning platform at a certain angle, and the radiation imaging system collecting a second projection image; and step 4: the radiation imaging system three-dimensionally reconstructing a sample structure based on the three projection images in step 1 to step 3.

Preferably, step 1 further includes:

step 11: the X-ray source emitting X-rays to the light source grating, and the light source grating dividing the X-rays into multiple coherent light sources;

step 12: the phase grating beam-splitting the X-rays emitted by the multiple coherent light sources, which produces incoherent interference and form interference fringes;

step 13: the analysis grating converting the phase information of the X-rays beam-split in step 12 to light intensity information of the X-rays, which are irradiated to the surface of the photon count detector; and step 14: the photon count detector counting photons of the X-rays reaching the surface, to form a reference image.

Preferably, step 2 or 3 further includes:

step 21: the X-ray source emitting X-rays to the light source grating, and the light source grating dividing the X-rays into multiple coherent light sources;

step 22: after X-rays emitted by the multiple coherent light sources penetrate the sample, phases of some of the X-rays changing;

step 23: the phase grating beam-splitting all the X-rays of which the phases change and do not change, which produces incoherent interference, to obtain deformed interference fringes;

step 24: the analysis grating converting the phase information of the beam-split X-rays in step 23 to light intensity information of the X-rays, which are irradiated to the surface of the photon count detector; and step 25: the photon count detector counting photons of the X-rays reaching the surface, to form a projection image.

A photon count-based radiation imaging system, including:

an X-ray source used for generating X-rays, an X-ray collimator used for restricting and adjusting widths and directions of X-ray beams, a photon count detector used for collecting ray signals produced when the X-rays penetrate an object, and a timing position controller used for used for synchronously controlling irradiation directions of the X-rays according to predetermined timing and activating corresponding partitions of the photon count detector;

wherein the X-ray source generates X-rays, which points to the activated partitions of the photon count detector after adjustment by the X-ray collimator.

Preferably, in the case of employing mechanical control, a mechanical motion device is further included;

wherein the timing position controller activates one partition of the photon count detector, the mechanical motion device adjusts the direction of the X-ray collimator according to a command of the timing position controller, and the X-rays generated by the X-ray source are adjusted by the X-ray collimator to form narrow X-ray beams, to make the narrow X-ray beams point to the activated partition of the photon count detector.

Preferably, in the case of employing electron control, a deflection mechanism and an electron-beam reduction target are further included;

wherein the timing position controller activates one partition of the photon count detector; the deflection mechanism adjusts a flight direction of an electron beam, and the electron-beam reduction target causes the electron beam to slow down suddenly and generate X-rays; and with the constraint of the X-ray collimator, the X-rays point to the activated partition of the photon count detector.

A photon count-based radiation imaging method, including:

(1) partitioning the photon count detector;

(2) the timing position controller activating one partition of the photon count detector, and shielding other partitions at the same time;

(3) the X-ray source generating X-rays, which point to the activated partition of the photon count detector after being adjusted by the X-ray collimator;

(4) the photon count detector collecting and recording data of the partitions; and (5) switching to another partition of the photon count detector, repeating steps (2)-(4), until data collection of all the partitions of the photon count detector has been completed, and obtaining suppressed images of scattered rays.

Compared with the prior art, the present invention has the following beneficial effects:

(1) the power of the X-ray source can be reduced, and the radiation on the patient is reduced;

(2) in the case of the lowest radiation, structural information inside a diseased area is collected, which may not lead to missed diagnosis;

(3) the data is collected at a faster speed, which is conductive to three-dimensional reconstruction; and (4) the system is miniaturized and is easy to maintain, which reduces the cost.

DETAILED DESCRIPTION

The technical contents of the present invention are further described below in detail with reference to the accompanying drawings and specific embodiments.

Figure 1:
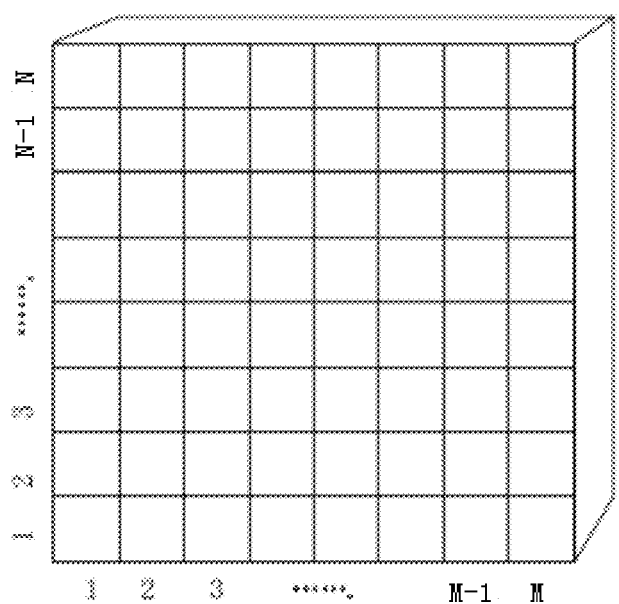
FIG. 1 is a schematic diagram of the appearance of a photon count detector according to the present invention.
Figure 2:
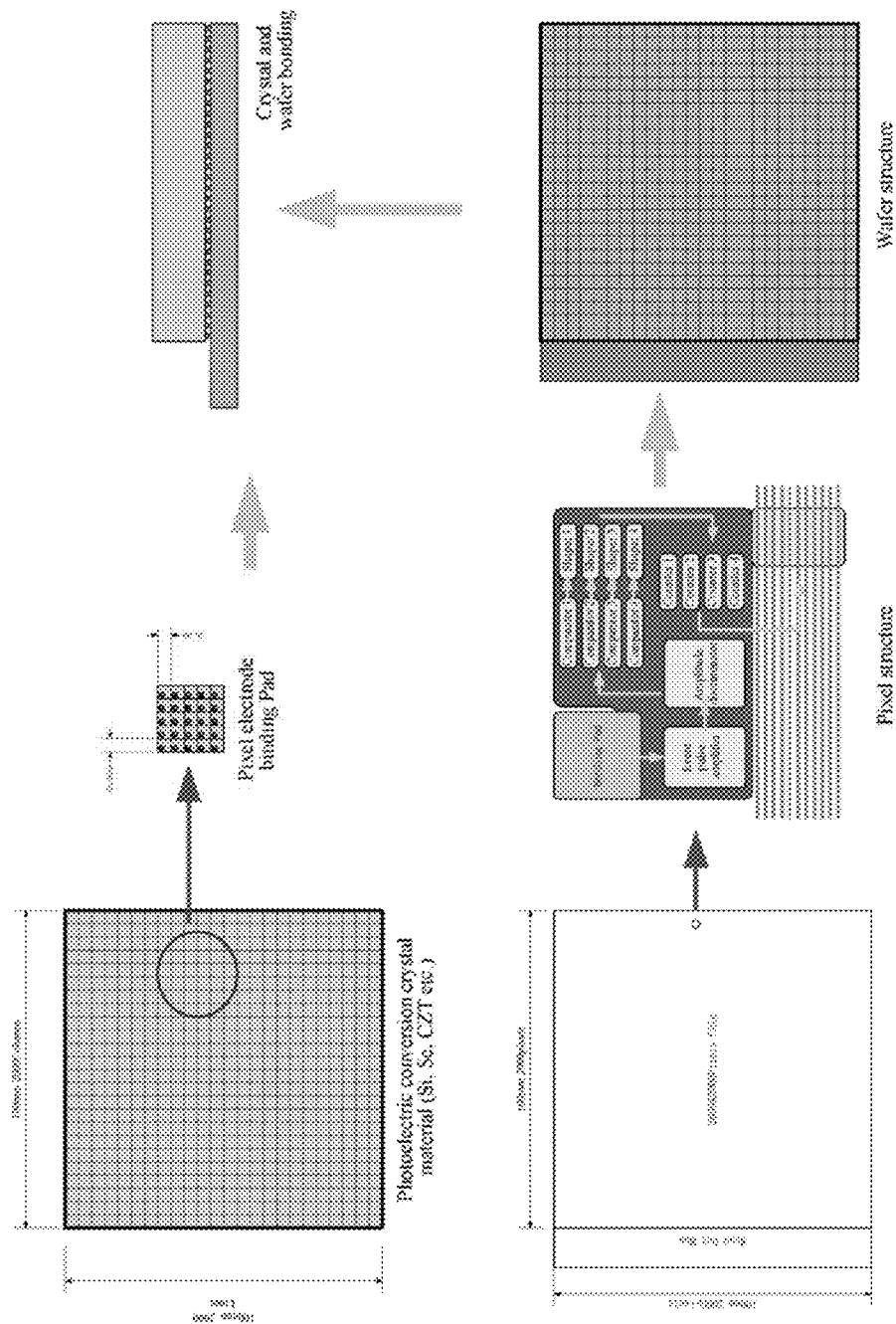
FIG. 2 is a schematic diagram of the structure and the size of the photon count detector according to the present invention.
Figure 3:
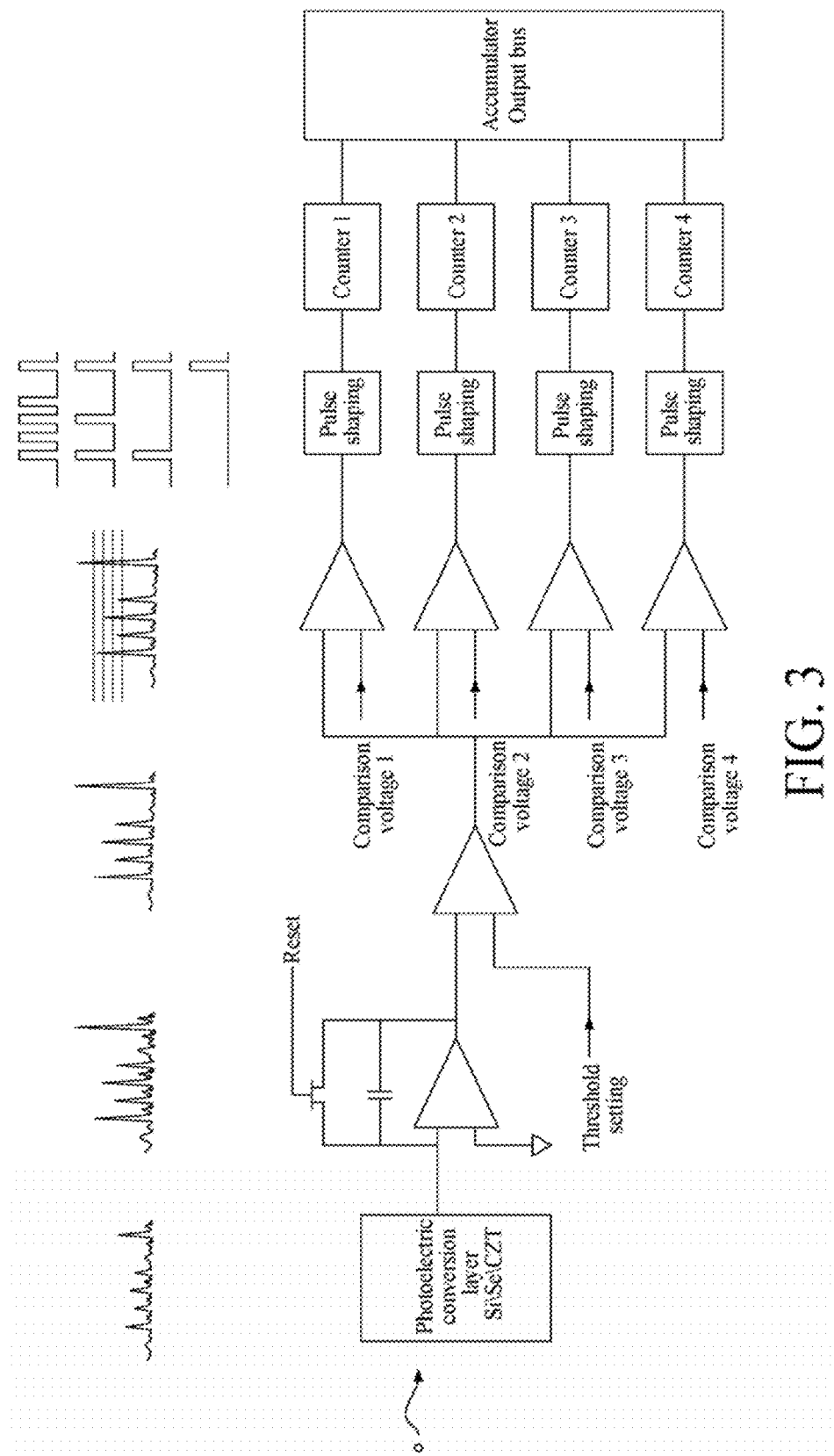
FIG. 3 is a functional block diagram of a pixel unit of the photon count detector according to the present invention.

FIG. 1 to FIG. 4 illustrate a new photon count detector according to the present invention. As shown in FIG. 1 and FIG. 2, the photon count detector is a plane-array structure made up of multiple pixel units. FIG. 3 illustrates a functional circuit diagram of each pixel unit of the photon count detector. Each pixel unit includes a photoelectric conversion layer, a pre-amplifier, an event detection unit, a level discrimination comparator, a pulse shaper, a counter, an accumulator and an output bus; wherein the photoelectric conversion layer converts a single photon to an electrical signal, and the electrical signal is transmitted to the pre-amplifier for amplification; the event detection unit filters noise in the electrical signal and sends the electrical signal to the level discrimination comparator; the level discrimination comparator grades effective signals which enter the pulse shaper for pulse shaping; and the counter counts pulse signals which are input to the accumulator and output to the output bus.

Figure 4:
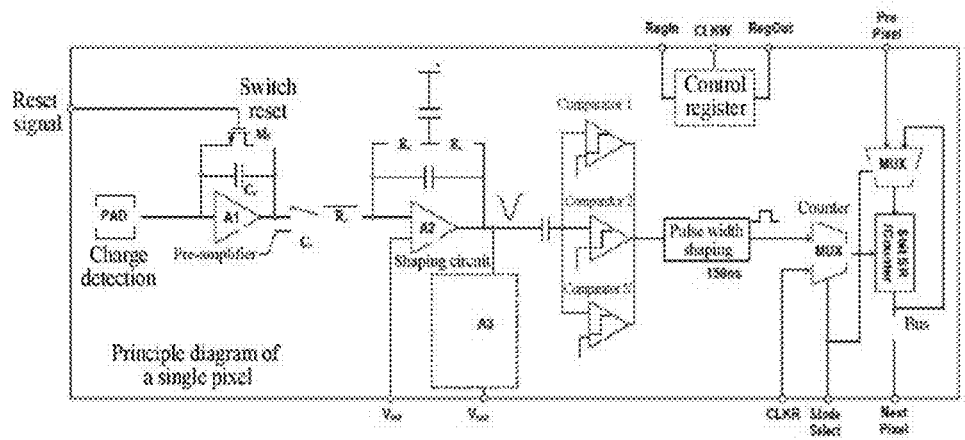
FIG. 4 is a schematic circuit diagram of the pixel unit of the photon count detector according to the present invention.

As shown in FIG. 4, the photoelectric conversion layer is connected to an input terminal of the pre-amplifier, an output terminal of the pre-amplifier is connected to the event detection unit, and an output terminal of the event detection unit is connected to the level discrimination comparator. In one embodiment of the present invention, the pre-amplifier, the event detection unit and the level discrimination comparator are all achieved by an operational amplifier and peripheral circuits thereof. The level discrimination comparator is achieved by four comparator circuits connected in parallel. The comparator circuits are respectively provided with a comparison voltage 1, a comparison voltage 2, a comparison voltage 3 and a comparison voltage 4 used as comparison references, and output terminals of the comparator circuits are connected with the pulse shaper and the counter sequentially. Output terminals of the four counters are connected with the accumulator and the output bus respectively. In addition, the detector unit may also be provided with several (generally 5) registers, wherein the total number of photon events is stored in one of the registers, and the number of photons at different energy levels is stored in others.

In the photon count detector according to the present invention, the photoelectric conversion layer is used for achieving conversion of optoelectronic signals, and the material used may be one of silicon, cadmium telluride, cadmium zinc telluride and selenium, which is not specifically defined in the present invention. In the photoelectric conversion layer, single X-photons are captured, and an electron hole pair is formed. The electron hole pair, under the action of an applied electric field, is transmitted to the input terminal of the pre-amplifier. The pre-amplifier pulse-amplifies a single photon event, which is handed over to the event detection unit for filtering noise. After the X-rays penetrate the sample, as atomic numbers of tested materials on the light path are different, energy of photons reaching the surface of the photon count detector varies, and event pulse amplitudes formed are also different. Event pulses and a set threshold are discriminated and compared, and low-energy pulses can be discriminated and filtered. The function of the level discrimination comparator is distinguishing an effective event pulse from random noise and threshold-comparing the effective event pulse. Suppose that the number of the level discrimination comparator is set as K (K is a positive integer), the energy of a single X-photon may be divided into K+1 level discrimination groups. After the effect of the pulse shaper on the output of each level discrimination comparator, the event pulse is shaped into one channel pulse output, in order to perform subsequent signal digital processing. After the effect of the pulse shaper on each level event pulse, the counter counts photon events at different levels. Within a set counting time cycle, photon events of each channel are accumulated, and the cumulative sum is concurrently transmitted to an external data processing device within a readout cycle of the output bus. The counting cycle differs between $1/10^8$ s and 1 s, which is decided according to sizes of photon streams and significant digits of the counter and is also set according to actual application. Bus readout of each pixel unit merely requires 1 clock cycle for concurrent transmission, all the counters are reset simultaneously with the readout, and next, photon events are counted continuously. The timing can be controlled, so as to be used in different application occasions. Duty ratios of the counting and the readout may also be adjusted. Data of each pixel unit includes the counting sum and the cumulative sum of multiple energy levels. The counting sum indicates photon event energy information on the pixel unit, and the cumulative sum indicates density-related absorption attenuation information obtained by the pixel unit.

Figure 5:
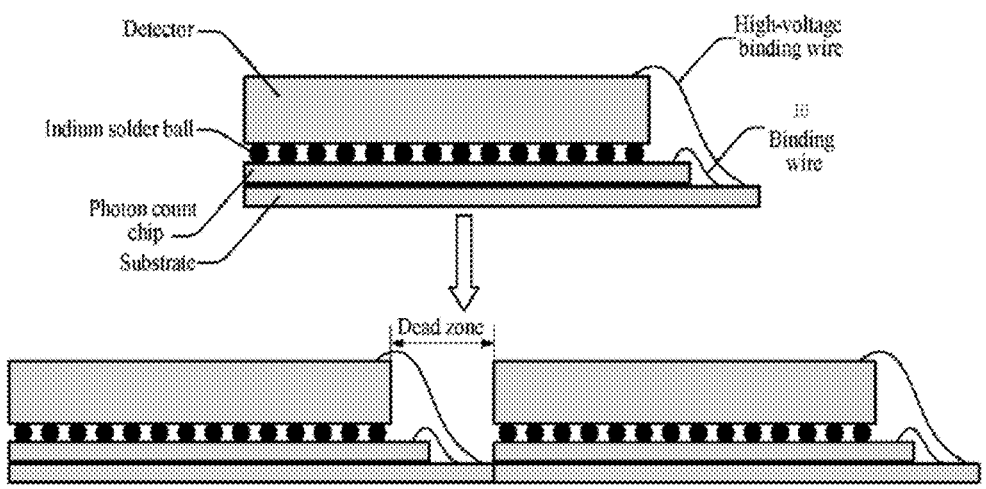
FIG. 5 is a schematic diagram of encapsulation and splicing of a photon count detector module in the prior art.
Figure 6:
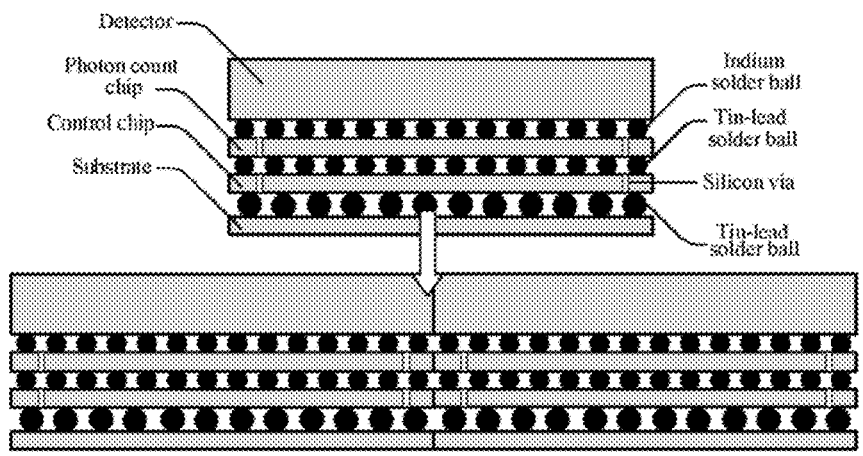
FIG. 6 is a schematic diagram of a multi-stack encapsulated photon count detector according to the present invention.

As shown in FIG. 5, when the photon count detector module performs array splicing, as enough space should be reserved for a routing area, a problem of splicing dead-zone definitely exists, and with respect to the above technical problem, the present invention provides a photon count detector. As shown in FIG. 6, the photon count detector provided in the present invention can achieve large-area plane seamless splicing, including a detector module, a photon count module, a control module and a substrate, and multi-stack encapsulation is achieved through methods such as a silicon via, indium solder ball flip-chip, tin-lead solder ball flip-chip and the like. The top layer is the detector module, which is connected with the photon count module on the lower layer through an indium solder ball. The photon count module in the present invention not only includes a pixel unit array, achieving functions of low-noise amplification of detector signals, threshold comparison, counting and data readout. The size of the photon count module is exactly the same as that of the detector module. Through the silicon via, a data input/output interface, a power supply interface, a bias interface, a control interface and the like of the photon count module are led out to the back of the photon count module, which is connected with the control module on the lower layer through an indium solder ball. The control module supplies power for the photon count module, provides a bias voltage, and completes a reading/writing function and an input/output buffer function. The control module also leads the input/output interface to the back of the chip through a silicon via technology, and then is connected to the substrate through tin-lead solder ball flip-chip. By use of such a multi-stack encapsulation form, the problem of splicing dead-zone of the traditional photon count detector can be solved, to achieve seamless splicing between the modules.

Figure 7:
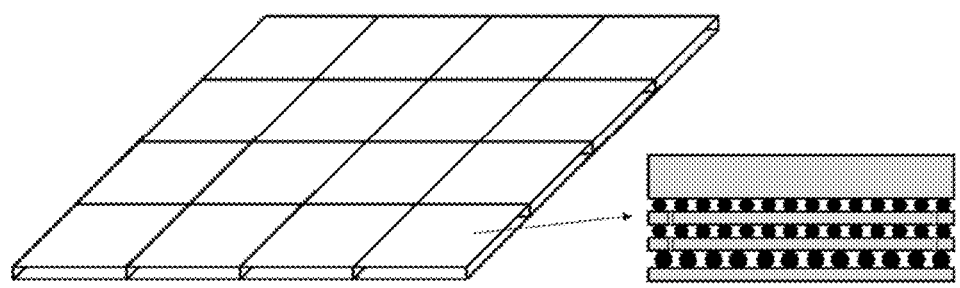
FIG. 7 is a schematic structural diagram of large-area plane seamless splicing of the photon count detector according to the present invention.

As shown in FIG. 7, considering that the detector module still needs to lead a high-voltage offset line out, if large-area seamless splicing is to be achieved, the detector module array can still only use the form of 2*N (N is a positive integer) array. The photon count module and the control module can use the form of M*K (M and K are positive integers) array. M=2*L, K=N*S (L and S are positive integers), that is, one detector module is flipped with L*S photon count modules. In one embodiment of the present invention, it is feasible to set N=2, L=2 and S=2, that is, each detector module and four photon count modules achieve encapsulation in the form of 2×2 array to form a photon count detector module, the size of each photon count module is 15 mm*15 mm, the size of each detector module is 30 mm*30 mm, and the size of each photon count detector module is 30 mm*30 mm. The photon count detector module is spliced according to the form of 2×2 array, and the size of the entire detector plane-array is 60 mm*60 mm. Such a large detector array plane can meet some imaging application demands, if it is necessary to increase the detector array plane, the detector module array should be ensured as in the form of 2*N, the size of the detector module can be increased to 60 mm*30 mm, each detector module is flipped with 4*2 photon count modules, to form a detector module with the size of 60 mm*30 mm, the detector module is used to perform splicing in the form of 2*4 array, and the entire detector array plane can be up to 120 mm*120 mm.

Figure 8:
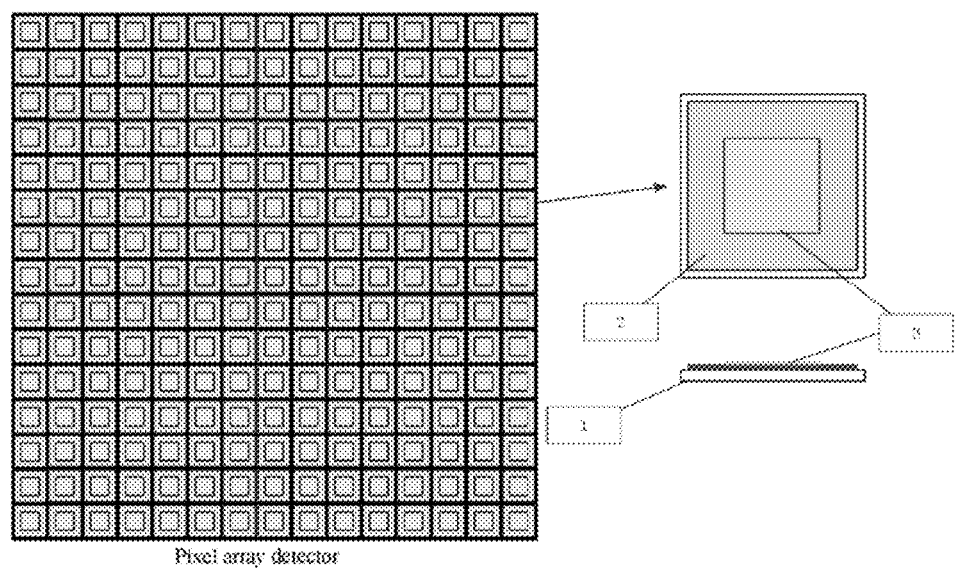
FIG. 8 is a schematic diagram of pins of the pixel unit of the photon count detector according to the present invention.

FIG. 8 illustrates a detector module structure. Each detector module is made up of a matrix type diode array. FIG. 8 gives a planar structure of a single PN-junction diode detector. In FIG. 8, the area denoted by the reference sign 1 represents an N-type substrate, the area denoted by the reference sign 2 represents a P+ doped area, and the area denoted by the reference sign 3 represents a positive-electrode pad. The N-type substrate is a common cathode of all diode arrays, and in an actual application, the common cathode is connected to a positive high-voltage end. In one embodiment of the present invention, the detector module is made of a high-resistance n-type silicon wafer, and according to an energy range of the X-rays to be detected, the thickness of the wafer may be selected as 300 μm, 500 μm, 700 μm, 1 mm or the like. The spacing of each pixel unit is 330 μm, the area of the P+ doped area is 300 μm*300 μm, and the area of the positive-electrode pad is 180 μm*180 μm. The entire detector module is in the form of 90*90 array, the area of the core pixel unit area is 29.7 mm*29.7 mm, the boundary of the pixel unit is at a distance of 150 μm from the edge of the detector module, and the size of the complete detector module is 30 mm*30 mm.

In one embodiment of the present invention, the photon count module array is 45*45, the size of the single pixel unit is 330 μm*330 μm, and the size of the entire chip is 15 mm*15 mm.

On the basis of the above photon count detector, the radiation imaging system and the radiation imaging method can be implemented in many manners. Detailed description is given below through different specific embodiments.

Embodiment 1

Figure 9:
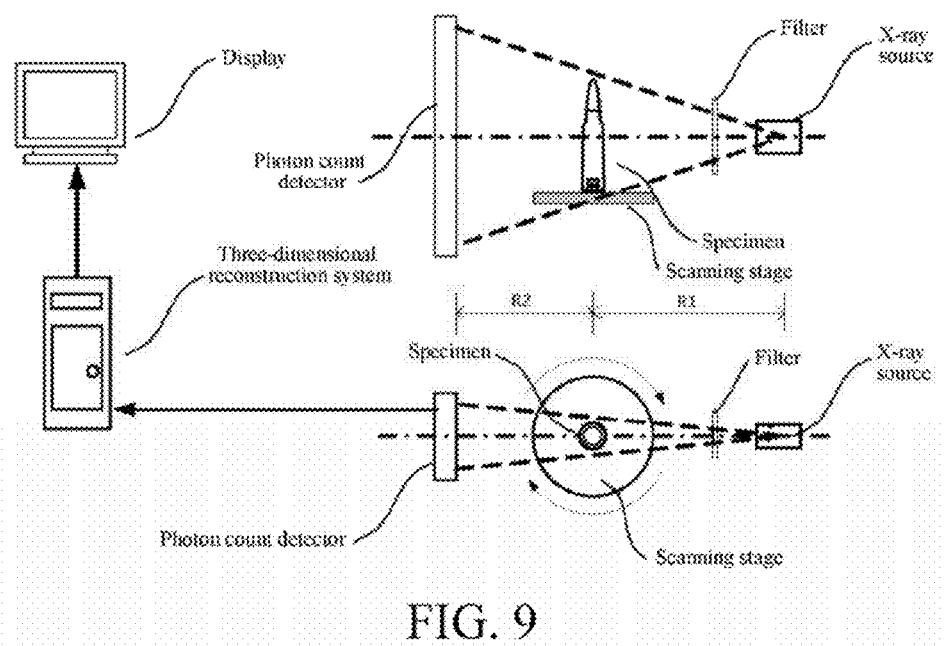
FIG. 9 is an overall schematic structural diagram of a photon count-based radiation imaging system in Embodiment 1 of the present invention, wherein the top right corner is another point of view of some components.

Embodiment 1 of the present invention provides a photon count-based radiation imaging system, as shown in FIG. 9, the radiation imaging system includes an X-ray source, a scanning platform for bearing a sample, a photon count detector, a three-dimensional reconstruction system and other components. The X-ray source is a micro-focus near monochromatic light source, used for emitting an X-ray to the sample on the scanning platform. After an X-ray is filtered by a filter, a near monochromatic X-ray is obtained and irradiated onto a tested sample. After the X-ray penetrates the sample, physical phenomena such as absorption, reflection, refraction, transmission, phase shift and the like may be generated, and lots of photons carrying material information in particular spatial positions are generated in an imaging plane. The photon count detector is used for counting photons in the imaging plane, so as to obtain projection data and energy data of incident photons, and transmits the projection data and the energy data to the three-dimensional reconstruction system. During irradiation of the X-ray, the tested sample continuously rotates and flips with the scanning platform, so that the three-dimensional reconstruction system acquires sample phase-contrast image sequences at different angles. The three-dimensional reconstruction system reconstructs phase distribution inside the sample according to the projection data; acquires pixel unit data blocks having an energy discrimination level, digitally dyes digital wax blocks of the sample according to an energy distribution map, and distinguishes matter composition inside the sample. By use of the radiation imaging system, submicron-level imaging can be achieved in pathology, histology, biology and industrial fields.

In the following, various components of the radiation imaging system according to the present invention are first described in detail.

The existing phase-contrast imaging method mainly includes an interference method, a diffraction enhancement method, an in-line method and a grating imaging method. In one embodiment of the present invention, the in-line method is used to perform phase-contrast imaging on the sample. As the in-line method is a non-interference phase-contrast imaging manner, a highly coherent or partially coherent X-ray source is required. To this end, a synchronous radiation source or a micro-focus X-ray tube needs to be employed.

Figure 10:
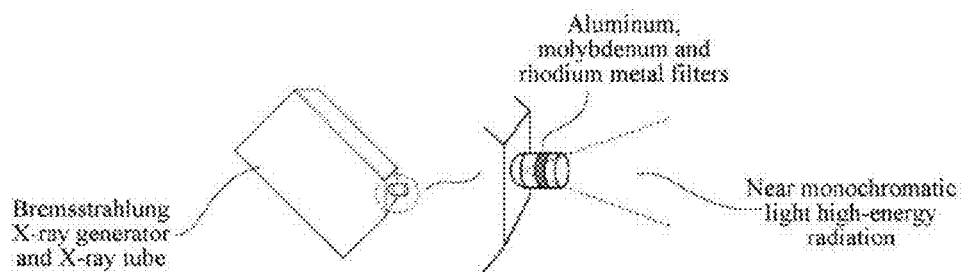
FIG. 10 is a schematic diagram of obtaining a near monochromatic X-ray after filtering of a filter.

In the present invention, the X-ray source used may include a synchronous radiation source, a micro-focus X-ray tube and so on. In consideration of factors such as the cost, the micro-focus X-ray tube is preferably used in the present invention. The micro-focus X-ray tube can control a light source focal point between 0.5 μm and 5 μm through bremsstrahlung. As shown in FIG. 10, in order to improve color purity of the X-ray, it is feasible to place a filter at the exit of the X-ray source, to filter out low-energy parts and high-energy parts, so as to obtain a near monochromatic X-ray.

Material selection of the target surface of the X-ray source and the filter plays a great role in the imaging effect of the sample. Generally, a metal material such as tungsten, molybdenum or rhodium is selected for the anode target surface of the X-ray source, and a metal material such as aluminum, molybdenum, rhodium or beryllium is selected for the filter. In one embodiment of the present invention, the anode target surface is preferably made of tungsten, and the filter is preferably made of one of aluminum, molybdenum, rhodium and beryllium. Such a combination manner not only can effectively reduce radiation dose of the X-ray of the living body such as human beings or animals and reduce potential damage to the living tissues, but also can ensure the imaging quality.

Figure 11:
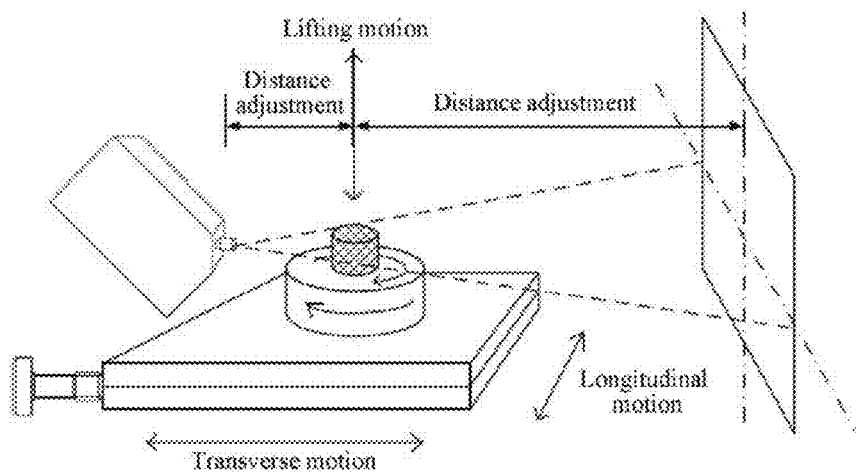
FIG. 11 is a structural example diagram of a scanning platform.

As shown in FIG. 11, the scanning platform used in the present invention can make the sample omnidirectionally rotate or flip thereon, to make it convenient to change the irradiation angle of the X-ray of the sample and obtain omnidirectional tissue structure information of the sample. The scanning platform may be achieved with the existing mature product, which is not specifically described herein.

Figure 12:
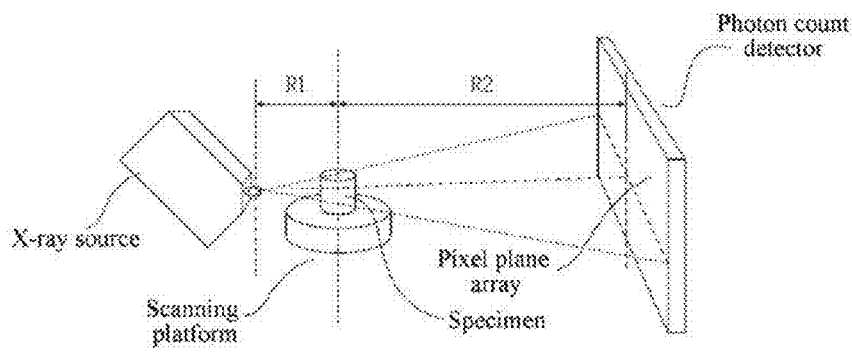
FIG. 12 is a schematic diagram of a geometry relation of cone-beam imaging, wherein the relationship among R1, R2, M and the size of the detector is shown.

The in-line method used in the present invention requires that the imaging plane must have an enough distance from the sample, and after the coherent X-rays penetrate the sample, the near-field Fresnel diffraction effect is generated. As shown in FIG. 12, to make the photon count detector imaged in a near-field Fresnel diffraction area, the following condition needs to be met: the distance between the focal point of the X-ray tube and the sample on the scanning platform is:

$$R1 = Ls * Fs / \lambda \quad (1)$$

Wherein Ls is a spatially coherent length, Fs is a focal point size, and λ is an X-ray wavelength. R1 can be properly adjusted according to the specification of the sample. Under normal circumstances, the spatially coherent length Ls is not less than 1 μm.

The distance between the sample and the photon count detector is:

$$R2 \approx \delta * \delta * M / \lambda \quad (2)$$

wherein λ is an X-ray wavelength, M is a magnification factor, M=(R1+R2)/R1, and δ is the detail to be identified by the sample. In practice, it is feasible to obtain a high-quality phase-contrast image corresponding to the identified detail by adjusting the size of R2.

Compared with the prior art, one notable feature of the present invention is replacing the traditional energy integral detector with the photon count detector. The photon count detector is a plane-array detector consisting of N*M (N and M are positive integers, generally not lower than 1024*1024, and can be more than 4096*4096 if necessary) pixel units, which is formed through a combination of an optoelectronic conversion device and an electrical signal processing circuit on a water level. The size of each pixel unit may range from 1 μm to 200 μm according to requirements of different application occasions for resolution. The size of the pixel unit ≤δ*M, δ is a detail to be identified by the sample, and M is a magnification factor; the matrix size=the sample size*M, for example, in the figure, the sample size is 5 mm, and the matrix size is 5 mm (sample size)*20=100 mm.

The photon count detector can obtain detection on each X-photon penetrating the sample at a very low dose, and discriminate energy of each photon. Specifically, the photon count detector obtains second-order differential phase shift information after the X-ray penetrates the sample, thus reconstructing a two-dimensional or three-dimensional image of the sample. Each pixel unit in the photon count detector serves as a detector unit and the pixel units are independent of each other. Each independent pixel unit has the capability of capturing, amplifying, discriminating, threshold-comparing, shaping and counting the single X-ray photon. The photon count detector counts photons of the imaging plane, measures photon energy on each spatial position through the energy discrimination unit inside the detector, and obtains projection data and energy data of incident photons of multiple parameters (at least including absorption contrast, phase contrast, single photon energy discrimination and the like).

The photon count detector conducts real-time communication through a common computer interface (including, but not limited to, a USB interface, a GB or MB network interface, a wireless network interface and the like), and data sending/receiving is performed line by line. Each line includes multiple pieces of information of N pixel units, each pixel unit includes the value of an intensity signal register and values of multiple level registers, and each frame includes M rows of data. After complete N*M frame image data is completely sent, the photon count detector sends head file information to a host computer. At a gap between frame images, the photon count detector and the host computer conduct a communication process of command parameters.

During operation of the photon count detector, each pixel unit measures intensity of captured photons, and obtains intensity information on the position of the pixel unit by recording the total number of the photons captured in a particular time window. The pixel unit, by comparing the threshold of each captured X-photon, can measure energy level of the X-photon. Generally, when the X-ray penetrates a particular tested material, the material with the higher atomic number absorbs more of the low-energy parts of the X-photon, the probability of passing of the low-level X-photon, and the probability that the pixel unit on the corresponding position captures a high-energy X-photon is higher. On the contrary, when the X-ray penetrates the material with the lower atomic number, the probability that a low-energy X-photon is detected is higher. In the case that the energy of the X-ray of the incident material is uniform, the X photon, after reacting with the materials having different atomic numbers, may also carry information indicating that energy varies. Through the energy discrimination function of the pixel unit, such difference can be detected. The difference belongs to the energy information mentioned hereinafter. In the traditional energy integral detection technology, what the detector measures is the sum of X-photon energy obtained by a single pixel unit within a period of time, while the photon count detector used in the present invention can discriminate energy of each photon reaching the pixel unit, thus obtaining multiple-level energy information. Owing to use of the photon count detector, it is feasible to cause the radiation imaging system to complete image acquisition at a very low brightness, and obtained intensity information can be used for image restoration of phase-contrast imaging; obtained energy information carries atomic weight and material density information of a tested sample, which can be used for digital dyeing of images. Such digital dyeing is performed based on material density and atomic weight, which includes a huge amount of information and far exceeds HE dyeing commonly used in histology and pathology at present (because dyeing is only performed based on pH values).

It should be stressed that the digital dyeing in this embodiment is different from the digital dyeing in the usual sense. In the prior art, the digital dyeing is achieved based on a dimension (intensity). The dimension used in reconstruction and the dimension used in dyeing are the same one (both are absorption values or referred to as intensity, and may also be referred to as CT values). The digital dyeing in the present invention is achieved based on different dimensions (mixed relations of multiple factors such as intensity, energy, a ratio or difference or product of intensity to energy). Owing to different dimensions, different dimensions must be used to collect a two-dimensional projection map (including phase-contrast image information, energy information and the like), and different dimensions are respectively reconstructed, and an arithmetical operation is performed on voxel parameters between the reconstructed different dimensions, to obtain a new dyeing parameter. For a photon count detector made up of N*M pixel units, each frame of data includes N*M absorption attenuation or phase shift information and energy information of N*M*(K+1) groups. X-ray photon intensity information collected on the imaging plane of the photon count detector and photon accumulated values of points of each pixel unit obtained through the counter form a projection map, and an energy distribution map is obtained through the level discrimination comparator.

The projection map is used for reconstructing the three-dimensional structure inside the sample, and the energy distribution map is used for identifying the matter composition of the sample. In terms of a two-dimensional angle, two-dimensional reconstruction can obtain an energy subtraction image, that is, an energy-related image can be obtained by subtracting a low-level image and a high-level image. By parity of reasoning, three-dimensional reconstruction can also obtain a three-dimensional voxel block that contains energy difference.

As the three-dimensional voxel block formed in this embodiment has multiple parameters, the function thereof and the "paraffin embedded tissues" made in the traditional pathology have the same meaning. During the post-processing, the three-dimensional voxel block including multi-parameter information is referred to as "digital wax block", it can be decomposed into two-dimensional slice images like the traditional pathology slice method and can exceed the concept of slice, digital image reconstruction of multiple physically drawn images is performed, including, but not limited to, surface feature drawing, endoscopic image drawing, extraction and drawing of particular structures (e.g., cell membranes, mitochondria, cell nucleus, chromosome and other organelles) and the like, and digital dyeing can be performed according to a unique multi-parameter (at least including absorption contrast, phase contrast, energy discrimination and the like of the tested material) dyeing technology.

The three-dimensional reconstruction system recovers phase-contrast information inside the sample according to the projection map and the energy distribution map of the photon count detector, and reconstructs the sample having a complicated internal structure by using a cone-beam three-dimensional reconstruction algorithm; according to a reconstruction result of the energy distribution map, and various parts of the internal structure of the sample are digitally dyed, to obtain matter composition information inside the sample. The digital wax block (i.e., three-dimensional voxel block) generated by the three-dimensional reconstruction system visualizes the internal structure and the matter composition of the sample and displays them intuitively through a display.

The three-dimensional reconstruction algorithm in this embodiment is specifically described below.

Figure 13:
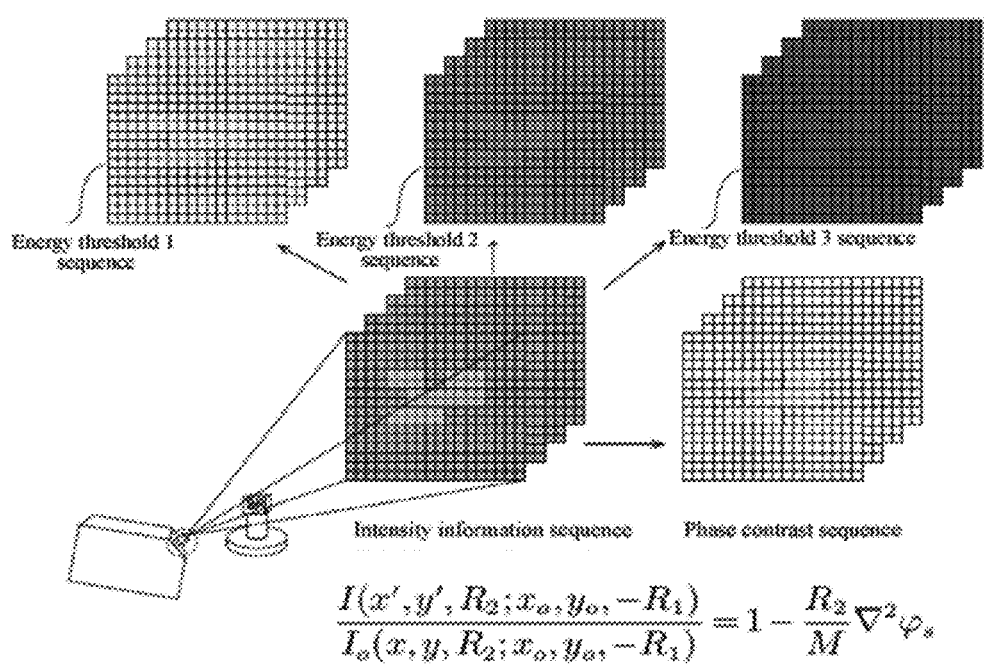
FIG. 13 is a schematic diagram of the working principle of phase-contrast imaging.

The scanning platform carrying the sample is rotated to a certain angle during each exposure of the X-ray, and the photon count detector collects a group of projection and energy data. After the sample completes 180°-360° rotation and exposure sequentially, the photon count detector obtains projection maps and energy distribution maps of the sample at various angles. The projection maps and energy distribution maps form a sequence atlas. The sequence atlas is three-dimensionally reconstructed, and it is feasible to obtain voxel data having sample material absorption, phase shift and energy information. X-ray photon intensity information collected on the imaging plane of the photon count detector and photon accumulated values of points of each pixel unit obtained through the counter form a projection map. The projection map is distribution of the phase contrast after Laplace transform, that is, edge contrast image. FIG. 13 shows the basic working principle of phase-contrast imaging.

$$\frac{I(x', y', R_2; x_o, y_o, -R_1)}{I_o(x, y, R_2; x_o, y_o, -R_1)} = 1 - \frac{R_2}{M}\nabla^2 \varphi_s, \tag{3}$$

Io(x, y, R 2; xo, y o, −R1) is the intensity value on an object plane; I (xo, yo, R2; xo, y o, −R1) is the intensity value on an imaging plane. Intensity and phase are directly related to Laplace transform, and after intensity information on the imaging place is measured, phase distribution on the object plane can be obtained through phase recovery (also referred to as phase distribution reconstruction). For phase recovery, the common algorithm in this field includes a TIE recovery method and an iterative restoration method. Reference can be made to the paper *Study on Micro focus X-ray Phase-contrast Imaging Phase Recovery Algorithms* (published on *Nuclear Electronics & Detection Technology*, Vol. 26, No. 6) written by Yu Aimin et al. for specific contents of the two algorithms, which are not repeated herein. In the present invention, the key of the in-line method lies in recovering phase contrast from the edge contrast image, thus obtaining phase-contrast distribution inside the sample.

In addition, the phase distribution reconstruction algorithm used by the three-dimensional reconstruction system may be divided to two categories: one is performing phase recovery first from projection data and then reconstructing phase (refractive index) distribution inside the object through the traditional filtered back-projection (FBP) or iteration method; and the other one is performing reconstruction directly, that is, a BR reconstruction algorithm is used, to directly three-dimensionally reconstruct phase distribution inside the object according to the fundamental theorem of in-line X-ray phase contrast CT proposed by Bronnikov (specifically refer to Bronnikov's paper *Phase-contrast CT: Fundamental theorem and fast image reconstruction algorithms*, published on *Proceedings of SPIE*, Vol. 6318, 63180Q). The two phase distribution reconstruction algorithms have been quite mature in this field, and are not described herein in detail.

Figure 14:
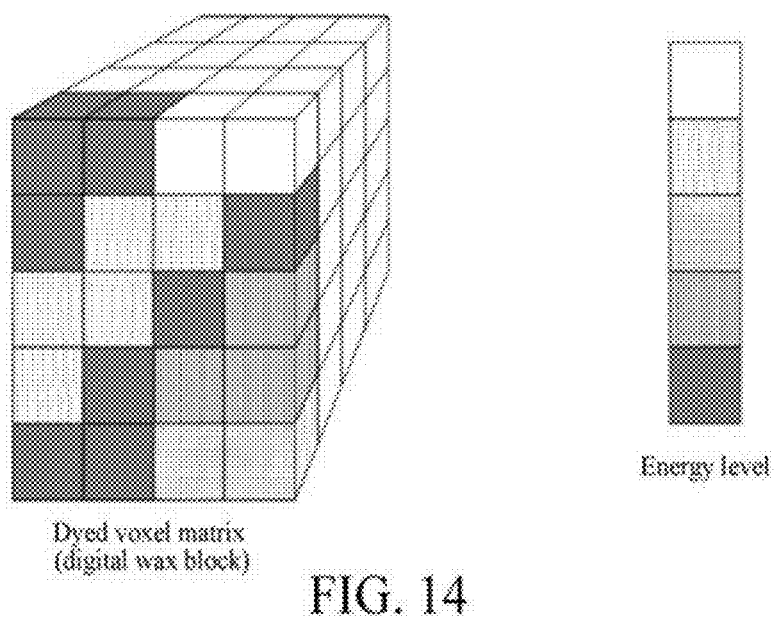
FIG. 14 is a schematic diagram of a digital wax block after digital dyeing.
Figure 15:
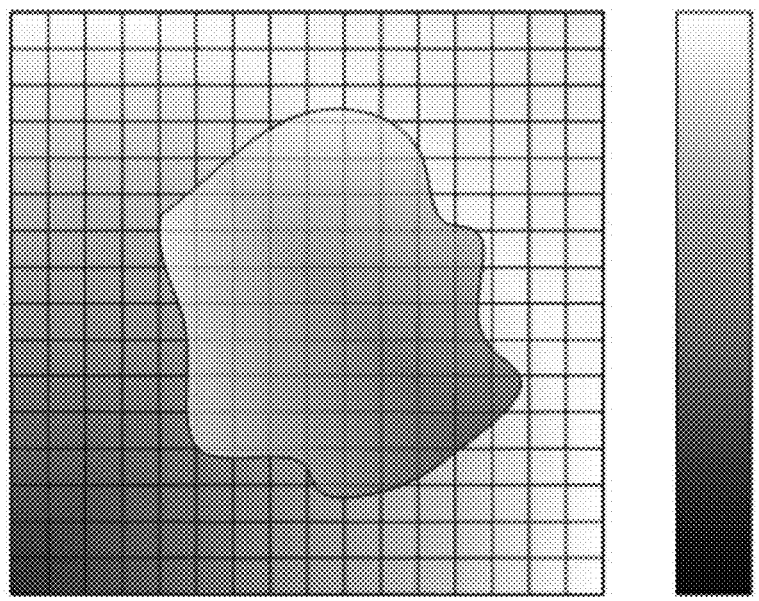
FIG. 15 is a schematic sectional diagram of digital dyeing using intensity information or phase information.
Figure 16:
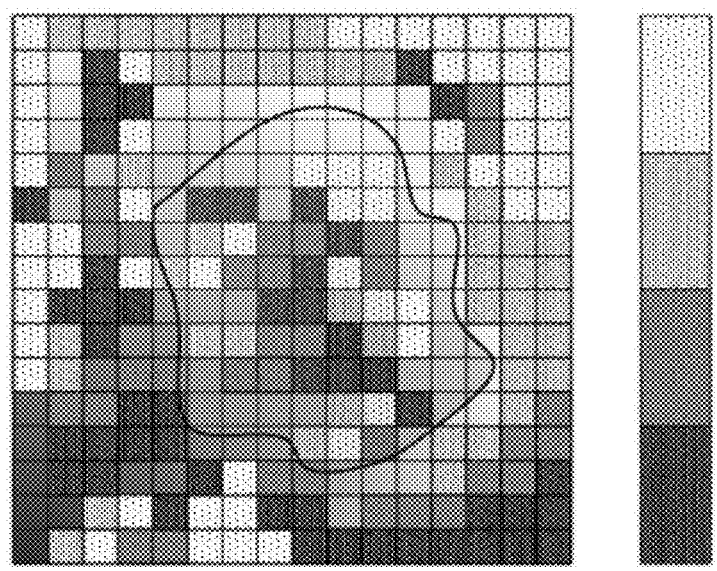
FIG. 16 is a schematic sectional diagram of digital dyeing to which energy level discrimination is added.

The three-dimensional reconstruction system obtains three-dimensional structure information inside the sample through phase distribution reconstruction, obtains three-dimensional energy distribution information inside the sample through energy distribution reconstruction, and digitally dyes components of the sample by using energy distribution volume data, to automatically classify matter composition information inside the sample. FIG. 14 is a schematic diagram of a digital wax block after digital dyeing. Herein, the energy distribution information is related to the energy level output by the X-ray source, and is also related to the material atomic number inside the sample. The atomic number of the tested material is determined according to absorption attenuation information of the material and the atomic number and ray energy of the material. The three-dimensional reconstruction system gives a corresponding color to the identified atomic number through digital dyeing, and displays the three-dimensional structure information and internal matter composition information through a display for an observer to analyze, specifically as shown in FIG. 15 and FIG. 16.

Figure 17:
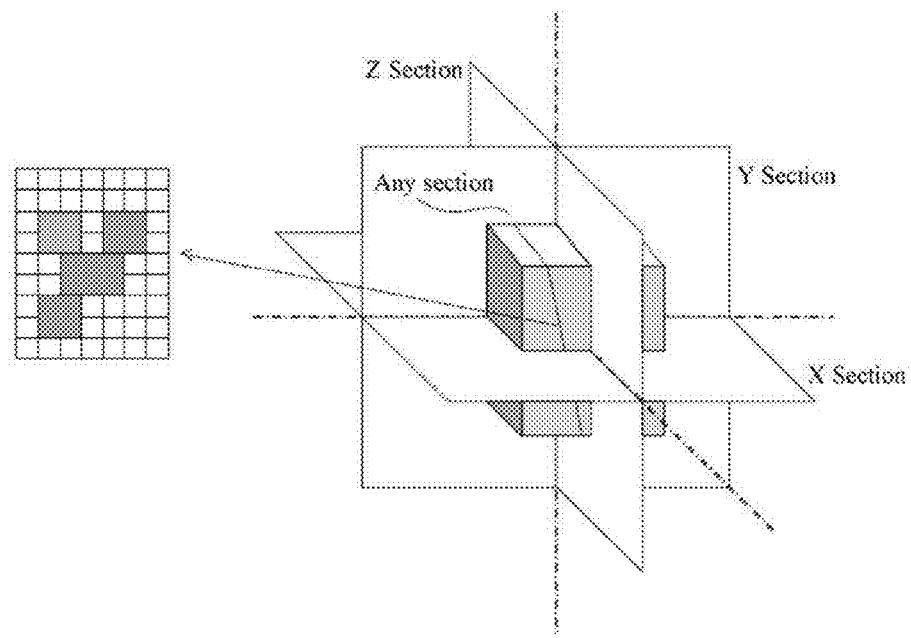
FIG. 17 is a schematic sectional diagram of obtaining any angle from a reconstructed digital was block.

As shown in FIG. 17, the three-dimensional reconstruction system digitally dyes and digitally slices the reconstructed digital wax block through spatial dimension information, phase information, energy information and density absorption information, and can provide a variety of image output forms, to make it convenient to observe and identify nuances of tissue structures; and obtains more kinds of different image output results by adjusting weights of various dyeing information parameters, to more provide internal information of the sample. Detection data generated in the reconstruction process, for example, two-dimensional data, three-dimensional data, digital dyeing parameters and so on, can be stored permanently, and can also be concentrated to a large data center through information exchange, to achieve data exchange and sharing, which is conductive to establishment of a diagnosis standard and experience exchange.

Specifically, the reconstructed digital wax block can obtain a section at any angle, on which intensity information on each pixel unit and energy level information are preserved, and it is feasible to perform digital dyeing on a slice level. Holographic information contained in the digital wax block includes three-dimensional reconstruction images related to intensity and energy distribution three-dimensional image data related to material atomic weight and density, and it is feasible to observe any section of a specimen through the digital slice at any angle; and different digital dyeing schemes can be used to digitally dye each pixel unit on the slice, including, but not limited to, dyeing according to intensity gradient, dyeing according to energy gradient and so on. In this way, more observation manners can be provided for the observer, including, but not limited to, a section image at any angle, a virtual endoscope image, a surface feature image of a particular structure, a decomposed or exploded image of a particular structure split and extracted and so on.

At present, the optical microscope relied on by the traditional histology and pathology has reached its limit in spatial resolution. This embodiment provides a new microexamination measure for non-destructive detection of biological soft tissues and pathological specimens, compared with observation of the traditional optical microscope and HE dyeing pathologic histology, the wavelength of the X-ray is 1-10 nm, the theoretical spatial resolution is 200-1000 times higher than that of the visible light, and the flaking process of the pathological specimens can be omitted, which is directly replaced with digital imaging.

Embodiment 1 can perform high-contrast imaging on weakly absorbing materials on the basis that low radiation doses and samples are not damaged. Compared with the traditional phase-contrast imaging technology, a photon count detector having energy identification capability is used in Embodiment 1, photon energy deposition is replaced with photon count, and for a low-brightness micro-focus X-ray source, the imaging time is shortened to about 1/10 of the imaging time of the traditional detector. In addition, the three-dimensional reconstruction technology used in this embodiment can obtain virtual slices at different angles, and can observe projection images, sectional images, three-dimensional reconstruction images of the specimens and their special dyeing effects; which greatly shortens the working procedure and the inspection report time of the conventional pathological section inspection. This embodiment meets the requirement of clinical application, develops new ideas and ways for applications of phase-contrast imaging towards medical, biological, industrial materials and other fields, and has important actual meanings and application values.

Embodiment 2

Figure 18:
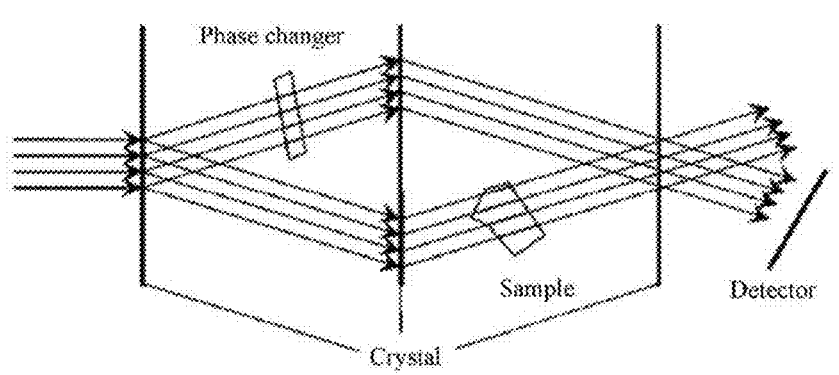
FIG. 18 is a schematic diagram of a basic light path of crystal interference contrast imaging.

In the X-ray imaging technology, a low-power-consumption micro-focus X-ray source is used, has enough coherence, but has a too narrow light beam and too small luminous flux, and the detector requires a quite long exposure time, which is limited to be extent during clinical application. As shown in FIG. 18, the present invention uses a grating self-imaging effect to design a light path, to cause an image of a first phase grating to match a second absorption grating, and then analyzes moire fringes formed by the sample, which can quantitatively recover a wave front. So, the present invention no longer relies on high-brightness and higher-coherence synchronous radiation light sources.

Figure 19:
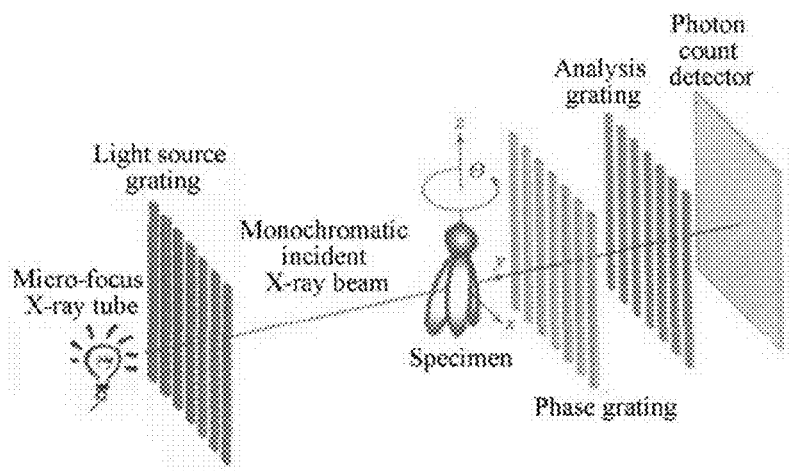
FIG. 19 is a schematic diagram of a grating shearing imaging device that extracts a horizontal refraction angle in Embodiment 2 of the present invention.

To this end, Embodiment 2 of the present invention provides a photon count-based radiation imaging system, and uses the photon count technology and the grating imaging technology to solve technical defects of the prior art. As shown in FIG. 19, it is an overall schematic structural diagram of a radiation imaging system. The radiation imaging system includes an X-ray source, a light source grating, a scanning platform, a phase grating, an analysis grating, a photon count detector, a three-dimensional reconstruction system (not shown) and other components. The light source grating, the phase grating and the analysis grating are in a plane structure, and may also be a surface structure with their centers at a light source side.

In this embodiment, the X-ray source is preferably a micro-focus near monochromatic light source, used for generating an X-ray. The X-ray is adjusted by the light source grating to obtain a coherent X-ray, and the coherent X-ray is irradiated onto a sample under test which is placed on the sample scanning platform. The light source grating is disposed between the X-ray source and the sample, and in order to have enough luminous flux, is provided with multiple very small gaps. The phase grating is disposed between the other side of the sample and the analysis grating, and the analysis grating is placed at a self-imaging distance, the function of which is similar to the function of the analysis crystal in the crystal diffraction enhancement method. By scanning the analysis grating in the direction of the X-ray, an intensity curve of different positions is obtained. The other side of the analysis grating is provided with the photo counting detector, the parts are arranged sequentially in a horizontal direction, and the photo counting detector is connected with the three-dimensional reconstruction system.

When the coherent X-ray penetrates the sample, physical phenomena such as absorption, reflection, refraction, transmission and the like may be generated, and lots of photons carrying material information in particular spatial positions are generated. The photons pass through the phase grating and generate phase change information (externally manifested as a moire fringe, and the phase change of the X-ray is displayed through a moving distance of the moire fringe). After the photons carrying the phase change information penetrate the analysis grating, by adjusting the position of the analysis grating, the phase information of the photons is converted to information of different light intensity on the photon count detector, and images formed on the photon count detector when the analysis grating is in different positions are recorded.

Figure 20:
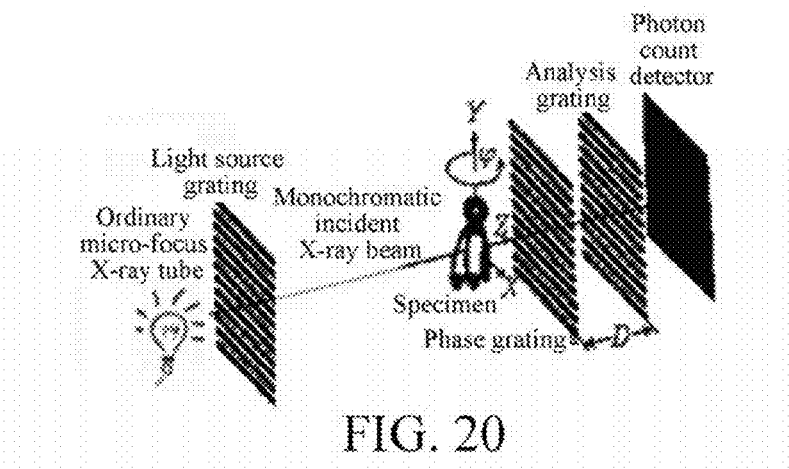
FIG. 20 is a schematic diagram of a grating shearing imaging device that extracts a vertical refraction angle in Embodiment 2 of the present invention.
Figure 21:
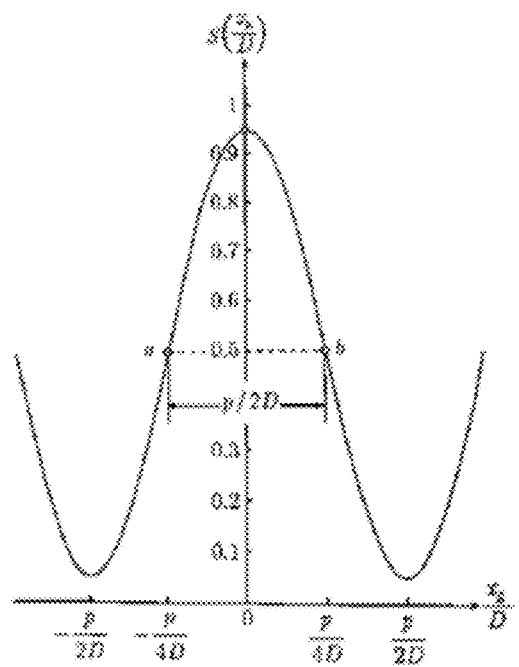
FIG. 21 is a schematic diagram of a displacement curve of an analysis grating in Embodiment 2 of the present invention.

When the radiation imaging system has no sample for detection, the coherent X-ray, after phase grating diffraction, will form a grating self-imaging fringe, and such a phenomenon is called Talbot effect (the effect can be regarded as a result of a combination of multiple double-slit interferences). As shown in FIG. 19 to FIG. 21, at the position of grating self-imaging, an analysis grating of which the spatial cycle is the same as the cycle of the grating self-imaging fringe. The analysis grating is an absorption grating, by adjusting the position of the analysis grating, grating self-imaging may pass and may not pass, and with lateral movement of the analysis grating, light intensity on the detector may present weak and strong cyclical changes. FIG. 21 is a curve that light intensity changes with the change of the position of the analysis grating, which is referred to as displacement curve because the curve is obtained by moving the analysis grating. To be able to propose a quantitative refraction angle signal, the simplest way is to form a linear relationship between analysis grating passing light intensity and the sample refraction angle. To this end, before the sample is placed, the position of the analysis grating is adjusted at first, to make the analysis grating and the grating self-imaging in a semi-alignment state, that is, the grating self-imaging can obtain a half of maximum passing rates on the analysis grating, which corresponds to a linear area of the displacement curve, that is, point a or b on the displacement curve in FIG. 21. In practice, the position is not limited to the points a or b, for example, it may also be trough and crest of the displacement curve, or other positions. After the sample is placed, the X-ray beam is irradiated onto the sample, the sample will generate positive or negative refraction angles in the horizontal direction and the vertical direction, the horizontal refraction angle may cause the grating self-imaging in FIG. 19 to produce horizontal lateral displacement, resulting in that the analysis grating passing light intensity in FIG. 19 linearly changes with the horizontal refraction angle, and the vertical refraction angle may cause the grating self-imaging in FIG. 12 to produce vertical lateral displacement, resulting in that the analysis grating passing light intensity in FIG. 20 linearly changes with the vertical refraction angle, and thus grating shearing imaging devices in FIG. 19 and FIG. 20 can be utilized respectively to obtain a refraction contrast image along the horizontal direction and a refraction contrast image along the vertical direction of the sample.

Figure 22:
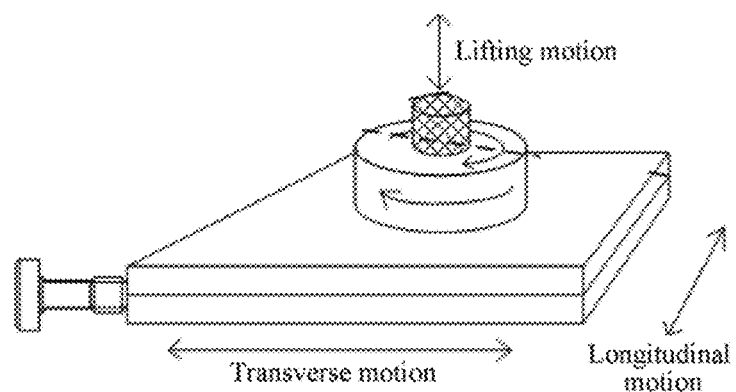
FIG. 22 is a structural example diagram of a sample scanning platform in Embodiment 2 of the present invention.

In this embodiment, the photon count detector in Embodiment 1 is used to count the photons on the imaging plane. Each pixel unit in the photon count detector serves as a detector unit, and the pixel units are independent of each other. Each pixel unit has the capability of capturing, amplifying, discriminating, threshold-comparing, shaping and counting the single X-ray photon, so as to obtain projection data and energy data of incident photons. The photon count detector obtains first order differential phase shift information after the X-ray penetrates the sample. During irradiation of the X-ray, the tested sample continuously rotates with the sample scanning platform. As shown in FIG. 22, the sample scanning platform used in one embodiment of the present invention can make the sample omnidirectionally rotate above the sample, to make it convenient to change the X-ray irradiation angle of the sample, obtain omnidirectional tissue structure information of the sample and transmit the information to the three-dimensional reconstruction system, so that the three-dimensional reconstruction system obtains sample phase-contrast image sequences at different angles, and the three-dimensional reconstruction system reconstructs phase distribution inside the sample according to the projection data, thus reconstructing a two-dimensional or three-dimensional image of the sample.

Embodiment 2 of the present invention provides a photon count-based radiation imaging system, which three-dimensionally reconstructs the structure of the sample based on a reference projection image in the absence of the sample and two projection images at different angles in the presence of the sample. The process of obtaining the projection image includes the following steps:

step 1: when there is no sample on the sample scanning platform, the radiation imaging system collecting a reference projection image;

step 2: placing a sample on the sample scanning platform, and the radiation imaging system collecting a first projection image;

step 3: rotating the sample scanning platform at a certain angle, and the radiation imaging system collecting a second projection image; and step 4: the radiation imaging system three-dimensionally reconstructing a sample structure based on the three projection images in step 1 to step 3.

When no sample is placed on the sample scanning platform, the step of collecting images includes:

step 1: the X-ray source emitting X-rays to the light source grating, and the light source grating dividing the X-rays into multiple coherent light sources;

step 2: the phase grating beam-splitting the X-rays emitted by the multiple coherent light sources, which produces incoherent interference and form interference fringes;

step 3: the analysis grating converting the phase information of the X-rays beam-split in step 2 to light intensity information of the X-rays, which are irradiated to the surface of the photon count detector; and step 4: the photon count detector counting photons of the X-rays reaching the surface, to form a reference projection image.

The methods of collecting images when the sample is placed and after the sample scanning platform rotates are identical, including:

step 1: the X-ray source emitting X-rays to the light source grating, and the light source grating dividing the X-rays into multiple coherent light sources;

step 2: after X-rays emitted by the multiple coherent light sources penetrate the sample, phases of some of the X-rays changing;

step 3: the phase grating beam-splitting all the X-rays of which the phases change and do not change, which produces incoherent interference, to obtain deformed interference fringes;

step 4: the analysis grating converting the phase information of the beam-split X-rays in step 3 to light intensity information of the X-rays, which are irradiated to the surface of the photon count detector; and step 5: the photon count detector counting photons of the X-rays reaching the surface, to form a projection image.

The radiation imaging system is further described below in detail.

The X-ray source may include a synchronous radiation source, a micro-focus X-ray tube, an ordinary X-ray tube, an X-ray laser and so on. In consideration of lots of factors such as the cost and the technical problem to be solved, the micro-focus X-ray tube is preferably used in one embodiment of the present invention.

Reference can be made to the following formula (4) for specific calculation of grating shearing phase-contrast:

$$I = I_0 e^{(-\sum_{i=1}^{n} \mu_i L_i)} \quad (4)$$

In the formula (4), $I_0$ is incident light intensity, I is X-ray light intensity received, L is the thickness of the sample along the light direction, and m is a linear absorption coefficient of the sample. The linear absorption coefficient is related to factors such as the sample density of the total atomic absorption section s and other factors, see the following formula (5):

$$m = r \frac{N_A}{A} s \quad (5)$$

In the formula (5): NA is a Avogadro constant, A is atomic mass, and r is material density.

It is set that the pipe flow of the X-ray tube is 1 mA and the high pressure is 35 kV, and the absorption coefficient of the air for the X-ray may be about 1.5, and the sample is water 5 mm thick. The light intensity allowed to pass by the grating is below 10%, the phase grating at least reduces the light intensity by 50%, and the analysis grating reduces the light intensity by 10%. Thus, upon arrival at the detector, the intensity of the X-ray may be reduced to $\frac{1}{1000}$ of the original one.

To form a phase-contrast image on the detector, a common technical measure is prolonging the exposure time, but this may introduce lots of noise signals and reduce image resolution. Some noise, for example, random noise, can be canceled by prolonging the sampling time, while some noise increases with increase of the sampling noise, for example, electronic noise, quantum noise and the like. It is thus clear that the problem of low light level imaging must be solved so as to further develop the grating phase contrast.

If the contrast of the phase-contrast image on the detector is to be enhanced, the problem of low light level imaging can be solved. In the following, the theoretical method of grating shearing phase-contrast imaging begins to be deduced from the Talbot effect; reference can be made to Liu Yijin's doctoral dissertation *Study on X-ray phase-contrast imaging and CT* (University of Science and Technology of China, 2009) for details.

It can be known from the Fresnel-Huygens Principle that the wave front reaching a certain position of an observation point is formed by superposition of secondary waves sent by various points on a certain previous wave front. The Fresnel diffraction formula may be written as:

$$\psi(\vec{r}) \propto \int\int_{crack\ area} E_{incident}(x', y') \frac{\exp(ik|\vec{r} - \vec{r}'|)}{4\pi|\vec{r} - \vec{r}'|} dx' dy' \quad (6)$$

wherein $\vec{r}$ is a position vector of an incident window plane, $\vec{r}'$ is a position vector in a detector plane, $E_{incident}$ is incident wavefront distribution, and (x', y') are coordinate values in the incident window plane.

For the grating refraction system, $E_{incident}$ is jointly determined by the incident wavefront and the transmittance number of the grating.

Particularly, the imaging space is limited to a two-dimensional plane. A grating transmittance function in an ideal situation may be written as $$t(x) = t_0(x) * \text{comb}(x/d)/d \quad (7)$$

wherein $t_0(x)$ is a transmittance function in a single cycle of the grating, * denotes convolution, and comb(x) is defined as a comb function and is the sum of a series of Dirac functions, that is, $$\text{comb}(x) = \sum_{n=-\infty}^{+\infty} d(x-n) \quad (8)$$

By substituting the grating transmittance function into the formula (5), the optical propagation after the indicant light penetrates the grating can be simulated. In this case, the condition of self-imaging is that light intensity distribution frequency spectrum on an image plane is equal to frequency spectrum of the grating rear-surface, and an expression of a self-imaging distance may be deduced as:

$$D_n = \frac{1}{\eta^2} \times \frac{n \times T_1^2}{2l} \quad (9)$$

wherein n is Tablot series, and is a natural number; Dn is an n-series Tablot distance; when the grating is a $\pi/2$ phase-shift grating or absorption grating, $\eta=1$; when the grating is a $\pi$ phase-shift grating, $\eta=2$; $\lambda$ is the wavelength of an incident X-ray; T1 is the cycle of the grating.

Figure 23:
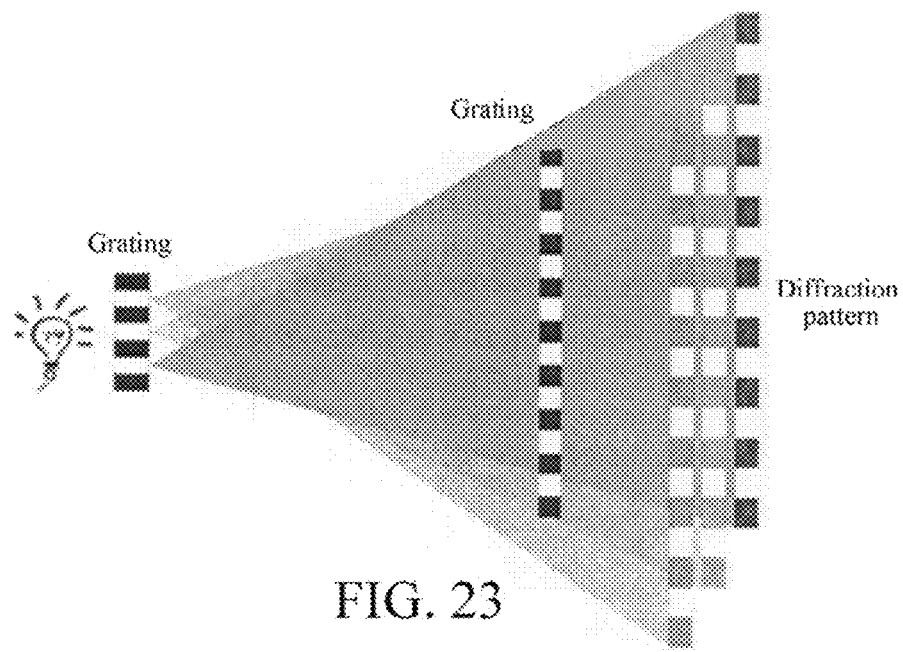
FIG. 23 is a schematic diagram of increase of grating imaging contrast after a light source moves.

In addition, due to lateral movement of the light source, it may lead to lateral offset of a self-imaging fringe, when the light source laterally moves at a proper distance, the self-imaging fringe may be dislocated an integral number of cycles and wholly incoherently superposed, the contrast of the fringe is enhanced, as shown in FIG. 23, in one embodiment of the present invention, X-ray light sources of two adjacent seams of the light source grating are not coherent, but interference fringes produced by the two adjacent seams are dislocated one cycle.

On the premise of not prolonging the exposure time, it is hoped that an enhanced phase-contrast image is formed on the detector. To further solve the problem of low light level imaging, a photon count detector is preferably used in the present invention. In this embodiment, the photon count detector of Embodiment 1 is used, and the structure and working principle thereof are not repeated herein one by one.

In this embodiment, only intensity information is received by the photon count detector, and the intensity information includes absorption phase and refraction angle phase (that is, phase shift), that is, the analysis grating changes phase information into intensity information. However, the parameter required by grating imaging is the refraction angle phase; therefore, to obtain the parameter, in two directions of p/4 (p is a cycle of a displacement curve of the analysis grating) and −p/4 or two directions of a phase difference of 180 degrees, it is necessary to shoot two images, a refraction angle is obtained from the two images, further, the phase information should be separated, a slice image based on phase contrast is established, and it is also necessary to establish a slice image based on absorption contrast, to fuse the two images together.

At present, shooting multiple projection images is the main trend of development, but the sample may be subject to excessive radiation, and imaging data collection time may be significantly prolonged, which is not in line with simple, rapid and low-dose requirements. In this embodiment, only by shooting two different projection images can the above technical problem be solved.

Figure 24:
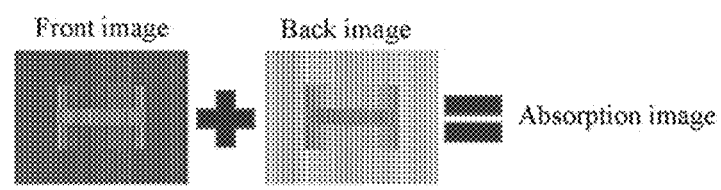
FIG. 24 is a schematic diagram of separation and extraction of an absorption image in Embodiment 2 of the present invention.
Figure 25:
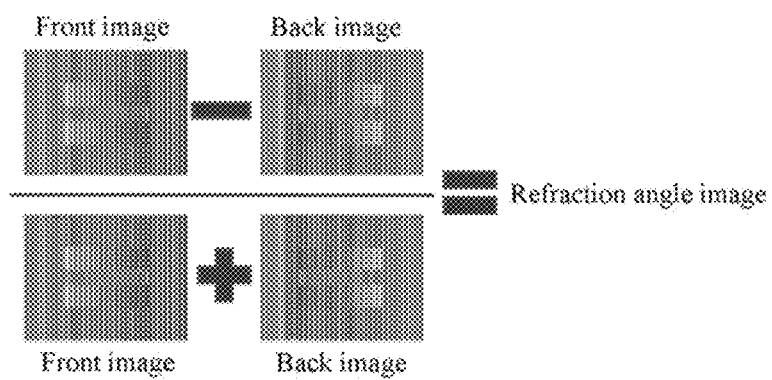
FIG. 25 is a schematic diagram of separation and extraction of a refraction image in Embodiment 2 of the present invention.

At first, according to the relationship between transmitted light intensity of the analysis grating and incident light intensity of the phase grating, the relationship between the transmitted light intensity of the analysis grating and incident light intensity of the sample can be obtained, and by moving the analysis grating to a certain position, light intensity linearly changes with the refraction angle and a formula thereof is obtained. In one embodiment of the present invention, after the sample is placed in the sample scanning platform, one image (front image) is shot for the sample, then, by taking Y axis as a rotating shaft, the sample is rotated 180 degrees, the other image (back image), rotation of the sample is not limited to 180 degrees, and when it is not 180 degrees, it is necessary to increase a calculation factor. As the front image and the back image have the same absorption attenuation and opposite refraction angles, mathematical expressions of two images can be obtained in the case that the rotation angle is not 180 degrees. Finally, mathematical formulas of the front image and the back image are added, to solve an absorption image of the sample, as shown in FIG. 24; a refraction angle image can be solved by dividing the difference of the two mathematical formulas by the sum thereof, as shown in FIG. 25. Reference can be made to *Synchrotron radiation light source and application thereof* complied by Mai Zhenhong (Science Press, March 2013, pages 658-660, ISBN: 9787030365347) for detailed deduction processes of the absorption image and the refraction angle image.

After the absorption image and the refraction angle image are obtained, three-dimensional imaging is performed in combination with the CT slice imaging theory. That is, a phase second derivative image can be obtained from the absorption image and the refraction angle image, and then a phase shift image is separated therefrom, and three-dimensional information is reconstructed by using the phase shift image, the horizontal refraction angle image, the vertical refraction angle image and the phase second derivative image. It is expanded from one slice to multiple slices, as the derivative of a phase factor under the coordinate system of the sample meets the characteristic of not varying with rotation of the sample, it is used as a reconstruction function, a filter back-projection reconstruction formula and a convolution back-projection reconstruction formula are further obtained, and title function reconstruction is extended to vector function reconstruction. Reference can be made to *Synchrotron radiation light source and application thereof* complied by Mai Zhenhong (Science Press, March 2013, pages 663-679, ISBN: 9787030365347) for the detailed deduction process of the three-dimensional reconstruction method.

Based on the above system and method, the following structural parameters are selected in one embodiment of the present invention, wherein an X-ray source, of which the focal spot diameter is not greater than 50 μm;

a light source grating, of which the grating constant is not greater than 10 μm and the grating area is 3 cm×3 cm; and the distance between the light source grating and the X-ray source is not greater than 2 mm.

This embodiment has the following effects: tissue forms less than 50 μm in the 1-mm sample can be identified, for example, identification of sweat gland follicles of skin tissues in pathological samples can be achieved; blood vessels less than 1 mm can be identified, to distinguish the interior and outer walls of the blood vessels; tiny calcified points less than 50 μm in 5 mm*5 mm*5 mm breast tissue samples can be identified, and homogeneity test of internal composition of 5 mm*5 mm*5 mm small pieces of organic materials is also available; the imaging time is shortened to 1/10 of the imaging time of the traditional detector.

The present invention combines the photon count detector with the grating phase-contrast imaging, can perform high-contrast imaging on weakly absorbing materials on the basis that low radiation doses and samples are not damaged, can well solve the problem that photons of the grating phase-contrast reaching the detector are fewer and long-time integral may introduce noise, and helps to further develop phase-contrast micro-CT.

Embodiment 3

As the grid of the X-ray source in the prior art has the following shortcomings: on the one hand, as the focal point of the grid is fixed, imaging requirements for different parts cannot be met, and the imaging quality is seriously affected; on the other hand, the grid per se also blocks some X-rays that should be shot to the photon count detector. In order to eliminate such adverse effects, radiation dose of the X-ray must be increased, which causes more radiation to tested objects especially patients and medical staff, increases the manufacturing cost of the photon count detector, and brings about difficulty to environmental protection work of the hospital.

As the virtual grid technology in the prior art does not filter scattered rays reaching the photosensitive plane of the photon count detector, scattered ray and straight ray data are all sampled. For the thick position radiography where scattered rays take a greater proportion, minor details of the straight rays have been "flooded" by lots of scattered rays when reaching the photon count detector, the minor details cannot be restored through software processing, and medical diagnosis requirements of thick position applications cannot be met.

There are some scatter correction methods in the prior art, which generates a scattering intensity distribution map by using a scatter corrector or an attenuation grid, and obtains a corrected projection image through a difference between a projection image and the scattering intensity distribution map. However, the scatter correction methods may double the scanning time, also double the data processing volume is also doubled, and have problems such as low efficiency and poor adaptability.

Therefore, to solve the above technical problems, Embodiment 3 of the present invention further provides a photon count-based radiation imaging system and method.

According to some known research results (specifically refer to a Chinese invention patent with Patent Number of ZL 200910022100.3), distribution of scattered rays may be approximately regarded as following normal distribution. For the one-dimensional situation, after one narrow-beam X-ray penetrates the tested object, intensity distribution of rays (including straight rays and scattered rays) on various positions of the x direction may be shown as the formula (10):

$$f(x) = \frac{1}{\sqrt{2\pi}\,\sigma} \exp\left(-\frac{(x-\mu)^2}{2\sigma^2}\right) \quad (10)$$

σ denotes the characteristic of the tested object, the size is determined by density and thickness thereof, and u denotes the position of the narrow-beam ray in the x direction.

Figure 26:
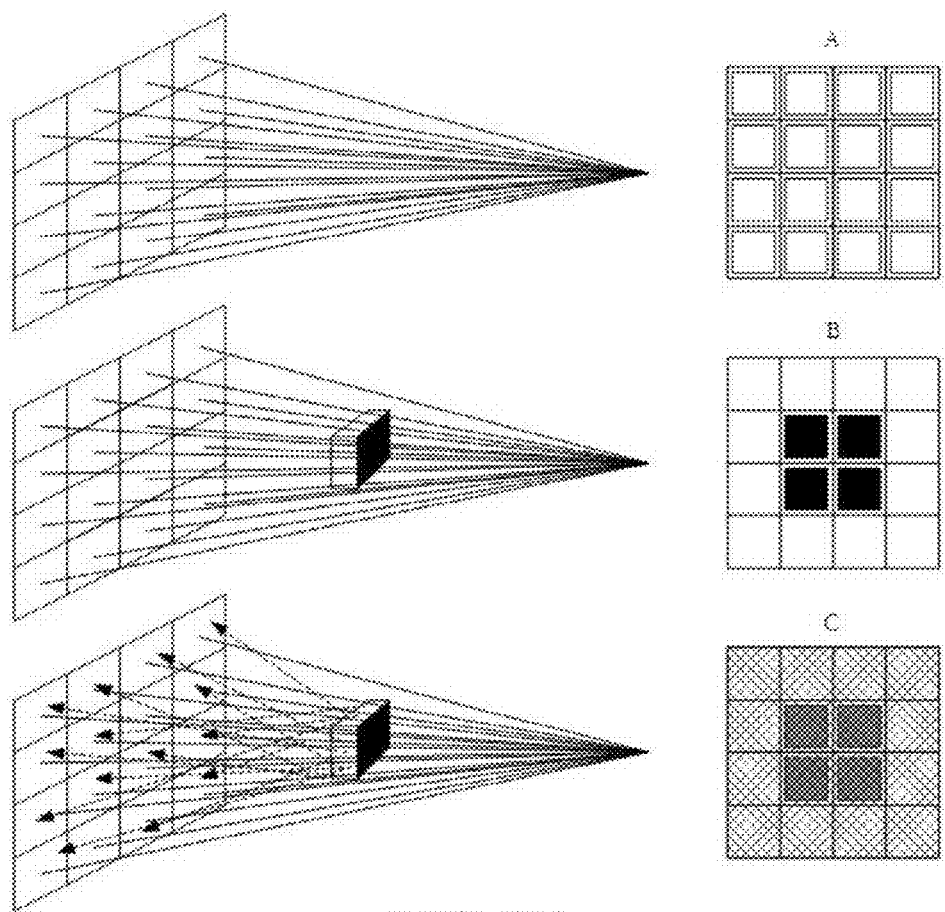
FIG. 26 is a schematic diagram of straight ray and scattered ray imaging.
Figure 27:
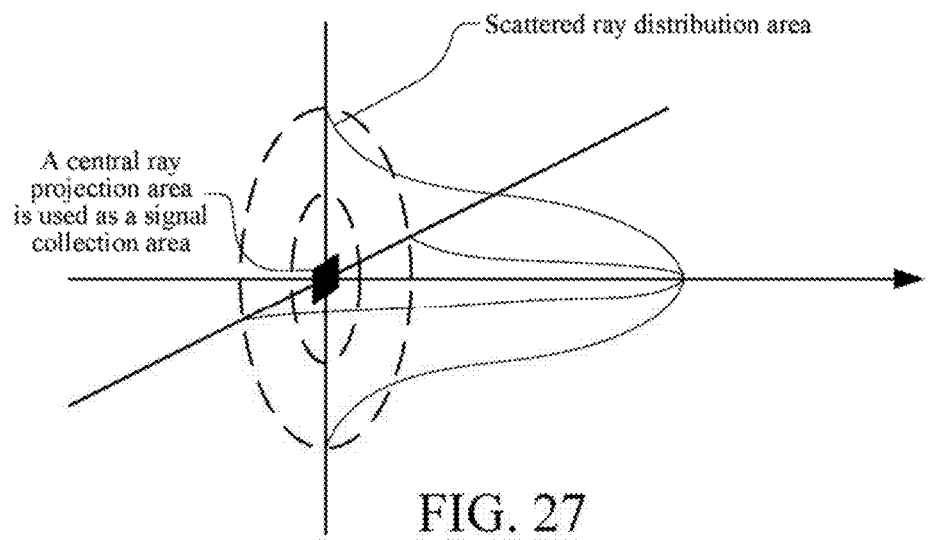
FIG. 27 is a schematic diagram of distribution of scattered rays.

As shown in FIG. 26 and FIG. 27, when straight rays from the focal point are transmitted to the photosensitive plane (preferably a scintillant coating and a thin film transistor array) of the photon count detector, scattered rays may be formed during the travel, thus forming the scattered ray distribution map shown in FIG. 26 and FIG. 27. The black block in the central position is a central ray projection area, and it is used as a signal collection area to collect straight rays from the focal point. The area represented by the circle around the central position is a scattered ray distribution area, and the scattered rays are mainly distributed in the area. In the present invention, to ensure the quality of collected images, it is necessary to perform certain processing on the scattered rays. Specific description is as follows:

The present invention uses an X-ray source performing scanning according to certain timing and a photon count detector that can control the collection position, by controlling the operation timing of the X-ray source and the photon count detector, ensures that only a small enough area obtains exposure of the X-ray in a moment, and only the pixel unit of the area of the photon count detector is in a collection state, while other pixel unit areas of the photon count detector are in a non-response state. In this way, the contribution of the scattered rays to an effective collection area will be reduced greatly. Theoretically, when the straight ray merely points to a single pixel unit and only the single pixel unit is in the collection state, the contribution of the scattered rays approaches zero. Still by taking one dimension as an example, the relationship between the contribution rate of the scattered rays and the size of the collection area can be represented with formula (11):

$$P(D) = \int_{m-D/2}^{m+D/2} e^{-\frac{(x-m)^2}{2\sigma^2}} dx \bigg/ \int_{-\infty}^{+\infty} e^{-\frac{(x-m)^2}{2\sigma^2}} dx \quad (11)$$

m denotes the position of the narrow-beam ray in the x direction; D denotes the collection width, taking m as the center; and P denotes the contribution rate of the scattered rays.

It can be known through the formula (11) that the smaller the collection width is, the smaller the contribution rate of the scattered rays is. In the case that only a single pixel unit or a small area collects directional X-rays at each moment while other areas do not collect X-rays, and scattering of X-rays in other directions affects scattering components of effective collection pixel units to be almost zero, signals collected by pixel units in an effective collection area (that is, effective collection pixel units) or a single effective pixel unit will be completely from straight rays.

Figure 28:
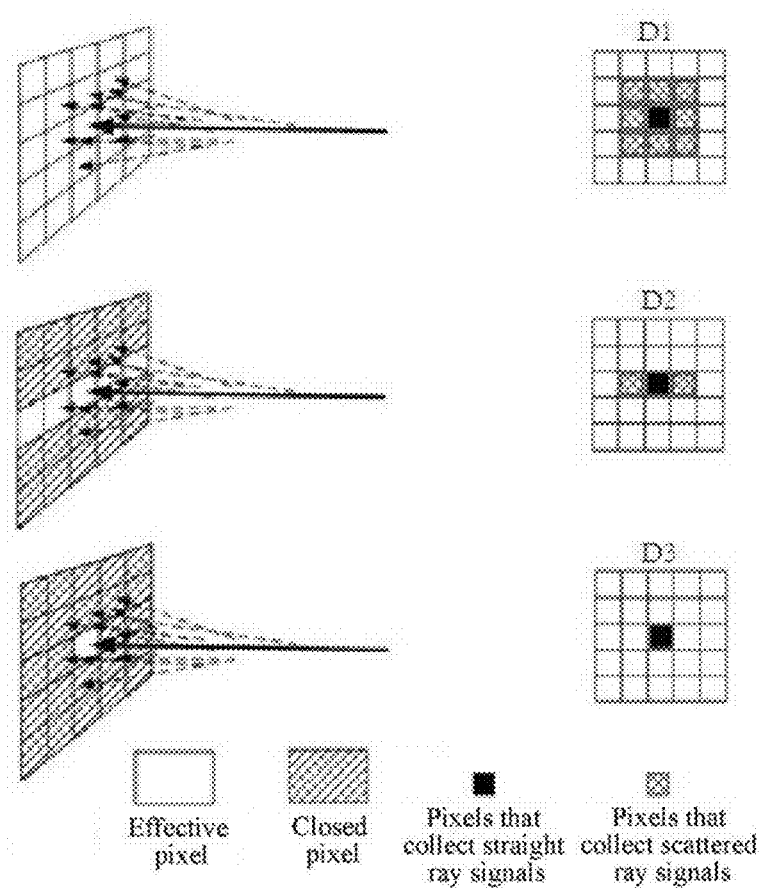
FIG. 28 is an effect diagram of influences of scattered rays when different pixel units are closed.

As shown in FIG. 28, single-beam X-rays are shot to different areas (pixel units or pixel unit blocks) on the photon count detector. The white square on the photon count detector represents an operating pixel unit, and the shaded square represents a pixel unit that has been closed but does not operate. In collected images D1-D3, the black square represents a pixel unit that collects straight ray signals, and the shaded square represents a pixel unit that collects scattered ray signals. The situation shown by the image D1 is the images collected by all the pixel units when in the operating state. When an X-ray is shot to the photon count detector, some rays may change directions to form scatted rays. When the X-ray reaches the photosensitive plane of the photon count detector, the situations of the pixel units affected are as shown by D1 in the figure. In addition that the pixel unit of the photon count detector collects straight rays, pixel units (that is, the shaded pixel units in FIG. 28) around the pixel unit may also collect signals of the scattered rays. The situation shown by the image D2 represents straight ray signals and scattered ray signals collected by the photon count detector when only one row of pixel units are activated and other pixel units are closed. Compared with the image D1, the scattered rays collected by the image D2 are evidently reduced. The situation shown by the image D3 is that the photon count detector does not acquire scattered signals when only one pixel unit is activated. In the present invention, collection is not necessary for the pixel units except the effective collection pixel units (that is, the pixel units shown by the black squares in FIG. 28), that is, the surrounding effective pixel units will not collect or transmit the scattered rays even if receiving the scattered rays. It can be known from theoretical derivation that, when a bundle of rays are limited to only exposing a single pixel unit, other pixel units can only receive scattered rays, while the pixel units that the bundle of rays face only have signals from primary rays, but scattered ray signals do not exist.

The radiation imaging system of this embodiment performs filtering and scattering by using a photon count detector and a time-sharing partition control manner, to increase the imaging effect, which includes an X-ray source, an X-ray collimator, a photon count detector, a timing position controller and other components.

(1) The X-ray collimator is used for restricting and adjusting widths and directions of X-ray beams. After the X-ray source is processed by the X-ray collimator, it is feasible to emit directional X-rays only to pixel unit areas (rows, points or small blocks) in the photon count detector which are in a state of responding to the X-rays, and straight ray parts of the X-rays will reach the pixel units in the photon count detector which are in a response state, while scattered rays will reach pixel unit areas which are in a state of not responding to the X-rays.

(2) The photon count detector can perform scanning and collection row by row, point by point or block by block in a time-sharing manner, in each time period, only one pixel unit or one small area (n*m pixel unit blocks, n and m are positive integers) is in a state of responding to the X-rays, while other pixel units or areas are all in a state of not responding to the X-rays.

(3) The timing position controller can control each area (row, point or small block) of the photon count detector to be in a collection state, control other partitions to be in a non-collection state (masked state), control X-rays emitted by the X-ray source to point to effective collection areas of the photon count detector, and ensure that no rays are emitted in other directions.

This embodiment further provides a photon count-based radiation imaging method, implemented based on the above photon count-based radiation imaging system, including:

(1) partitioning the photosensitive plane of the photon count detector;

(2) the timing position controller activating one partition of the photon count detector, and shielding other partitions at the same time;

(3) controlling the X-ray source to emit X-rays, which point to the activated partition after being restricted by the X-ray collimator;

(4) the photon count detector collecting and recording data of the partition; and (5) switching to another partition of the photon count detector, repeating steps (2)-(4), until data collection of all the partitions of the photon count detector has been completed. Thus, a complete scattered image can be obtained.

In this embodiment, the timing position controller partitions the photosensitive plane of the photon count detector according to the control mode selected by the user, and synchronously controls radiation directions of the X-rays according to partitioning results and activates corresponding partitions of the photon count detector. In this embodiment, a preferred scheme is that the timing position controller consists of a dot frequency generation circuit, a point counting circuit, a row counting circuit, a frame frequency control circuit, a detector timing control output circuit, an X-ray position control output circuit and the like. The circuits can be formed by slight transforming the timing controller or the timing control circuit in the existing CRT display. As a conventional technology that can be grasped by those skilled in the art, the circuits are not specifically described herein.

The radiation imaging system provided in this embodiment can employ two control modes: a mechanical control mode and an electronic control mode. Specific technical contents of the two control modes are specifically described below in detail respectively.

Figure 29:
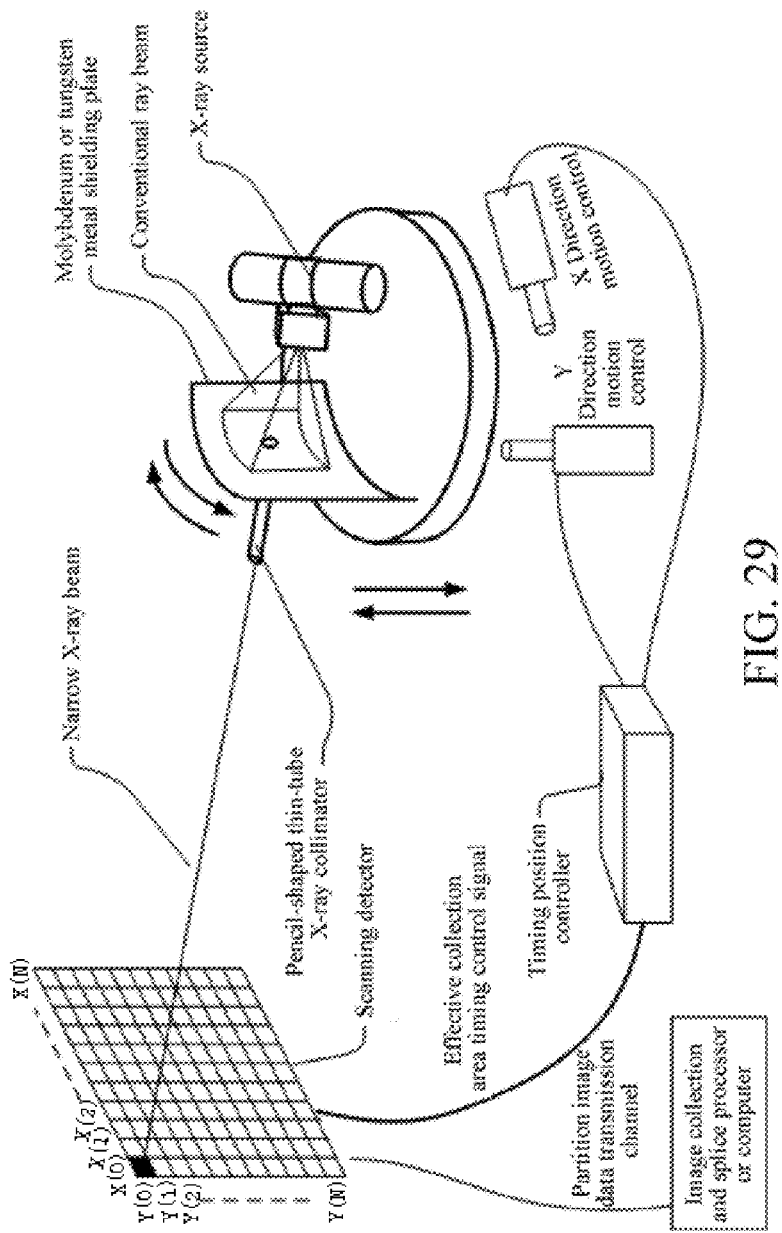
FIG. 29 is a schematic diagram of a radiation imaging system that employs mechanical control in Embodiment 3 of the present invention.

As shown in FIG. 29, when the radiation imaging system of this embodiment employs the mechanical control mode, a corresponding mechanical motion device is further included. The photon count detector may be used in a time-sharing and partitioning manner, that is, the photon count detector uses a pixel unit as the minimum unit, and it is feasible to use a single pixel unit, it is also feasible to use a single row of pixel units or multiple rows of pixel units, and it is also feasible to use a pixel unit block formed by several adjacent pixel units; the mechanical motion device includes drive motors in the X direction and the Y direction (or X direction, Y direction and Z direction), and thus under the guide of a control command, it is feasible to move in the X direction and the Y direction; the X-ray collimator is specifically a pencil-shaped thin-tube X-ray constraint in this embodiment, used to constrict X-rays to make the X-rays form a narrow X-ray beam. It can move under the control of the mechanical motion device; and the timing position controller is used for partition-activating the photon count detector according to certain timing.

Figure 30:
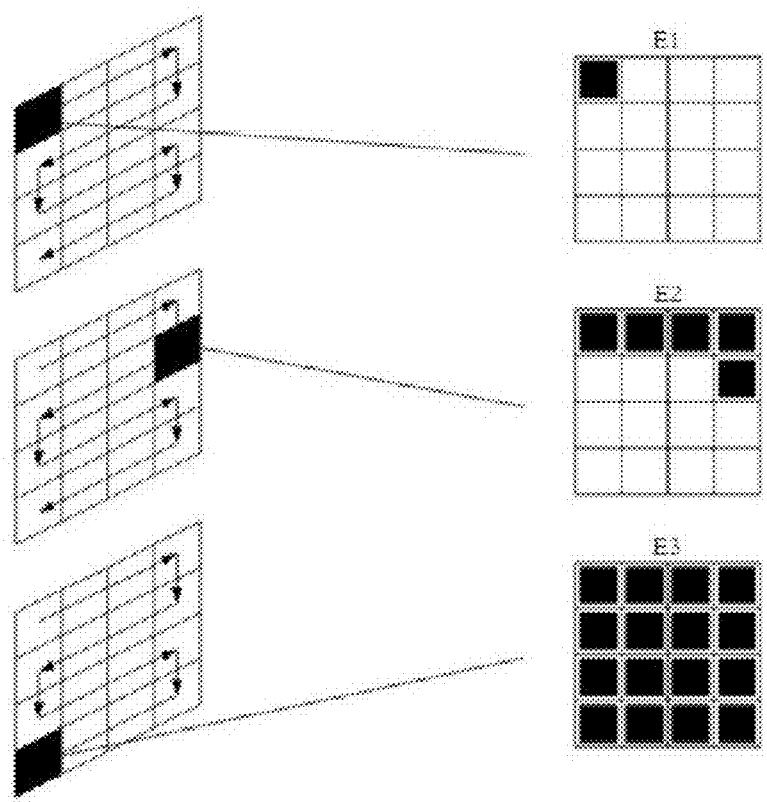
FIG. 30 is a schematic diagram of an image collection process in Embodiment 3 of the present invention.

In the case of the mechanical control mode, the working principle of the radiation imaging system is as follows: the X-ray source obtains a small enough narrow X-ray beam through a pencil-shaped thin-tube X-ray constraint, points to an activated area of the photon count detector, and only exposes one particular position within unit time. Within the unit time, the corresponding pixel unit in the photon count detector is notified to perform activation through a position signal, and signals of the area are collected. As shown in FIG. 30, the pencil-shaped thin-tube X-ray constraint, under the control of the mechanical motion device, moves along the X positive direction through the drive motor in the X direction, and synchronously moves with the activated area of the photon count detector, until all the pixel units in the X positive direction are completely exposed. Next, the drive motor in the Y direction is moved to a height of one area along the Y direction, to continuously perform scanning and exposure in the X negative direction. After walking all the way in the Y direction, each area of the photon count detector is completely exposed. The exposure process ensures that, under the directing of each mechanical motion, merely the directed pixel unit is activated, and ensures that only the activated pixel unit can collect and transmit straight X-ray signals, while other pixel units are in a closed or non-activated state and may not collect or transmit scattered rays received around.

Figure 31:
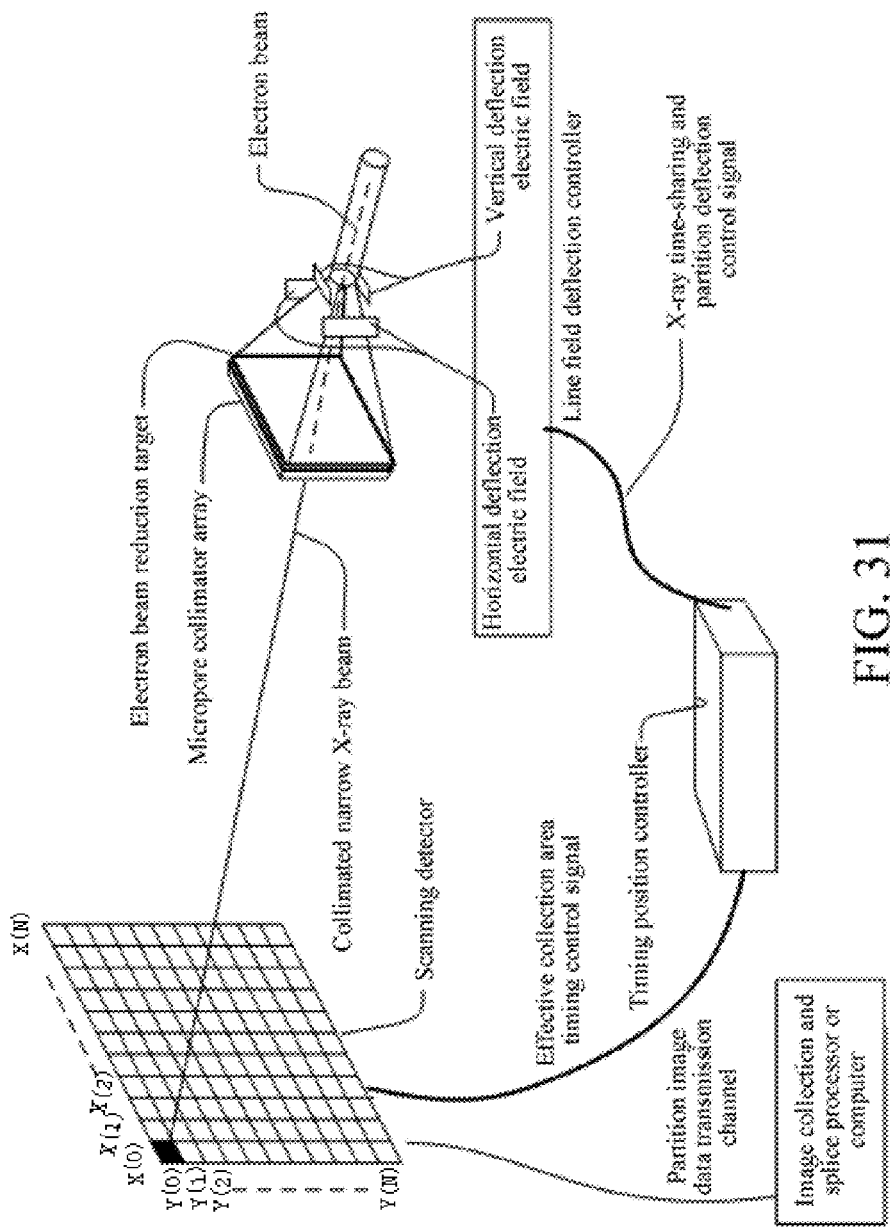
FIG. 31 is a schematic diagram of a radiation imaging system that employs electronic control in Embodiment 3 of the present invention.

When the radiation imaging system provided in this embodiment employs the electronic control mode, as shown in FIG. 31, an electronic gun, an electron-beam reduction target and a deflection mechanism. The photon count detector can be used in a time-sharing and partitioning manner, that is, the photon count detector uses a pixel unit as the minimum unit, and it is feasible to use a single pixel unit, a single row of pixel units or multiple rows of pixel units, and it is also feasible to use a pixel unit block formed by several adjacent pixel units; the X-ray source is replaced with an electronic gun in this embodiment. The electronic gun is used for emitting electron beams. The electron beams are controlled by an electromagnetic field, and the movement direction thereof can be adjusted. The deflection mechanism is used for adjusting the directions of the electron beams and making them point to corresponding partitions; the electron-beam reduction target (e.g., tungsten target or molybdenum target) is disposed in a vacuum environment, used for making the electron beams suddenly slow down and generating X-ray beams during reduction of the electron beams; the X-ray collimator is specifically a micropore collimator (also referred to as a partition collimator), disposed behind the electron-beam reduction target, used for collimating the X-ray beams; and the timing position controller is used for partition-activating the photon count detector according to certain timing.

Figure 32:
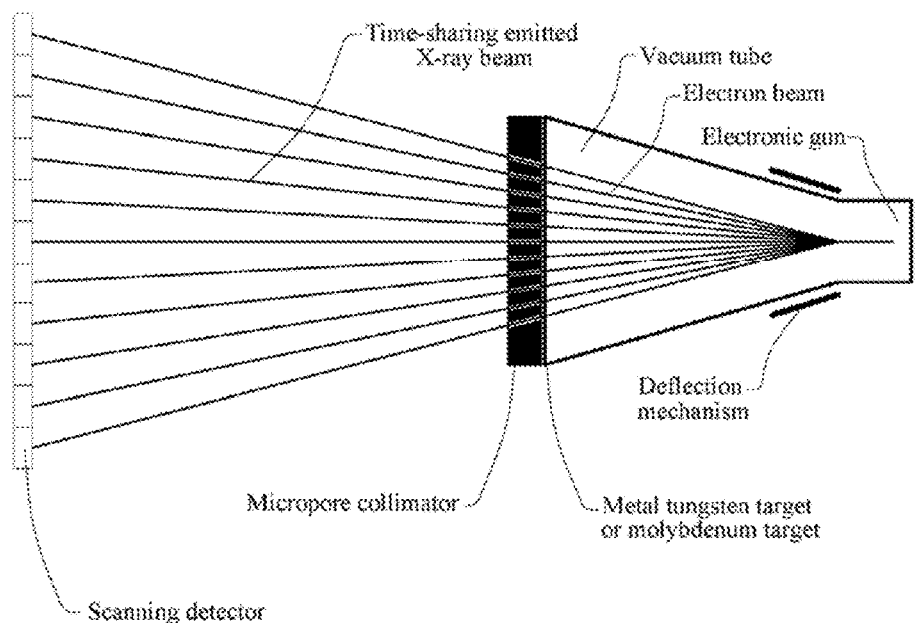
FIG. 32 is a schematic structural diagram of an electronically controlled X-ray source in Embodiment 3 of the present invention.

As shown in FIG. 32, when the radiation imaging system employs the electronic control mode, the working principle is as follows: through the command of the timing position controller, electrons emitted by the electronic gun form an electron beam, which deviates from the original movement direction under the action of the deflection mechanism, bombards the tungsten target in the corresponding area and generates X-rays, the X-rays pass through the micropore collimator and points to a first area of the first row on the photon count detector, and the timing controller activates pixel units in the first area of the first row on the photon count detector at the same time, to acquire non-scattered images of the first area of the first row. At this point, pixel units adjacent to the activated area may be subject to radiation of scattered rays, and as the pixel units are not activated, information of the scattered rays are not collected and transmitted. According to the timing command of the timing position controller, the photon count detector will complete collection of remaining areas of the first row one by one. When the pixel units of the first row are completely collected, pixel units of the second row are collected inversely and so on, until pixel units of all the rows are completely collected, thus obtaining a clean image where scattered rays are suppressed. The process is the same as the line of collecting images in the case of mechanical control mode, and is not repeated herein.

Figure 33:
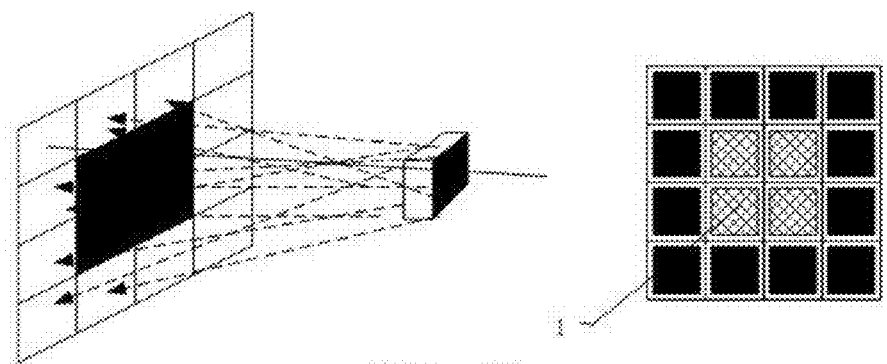
FIG. 33 is a schematic effect diagram of images collected by the radiation imaging system in the prior art.
Figure 34:
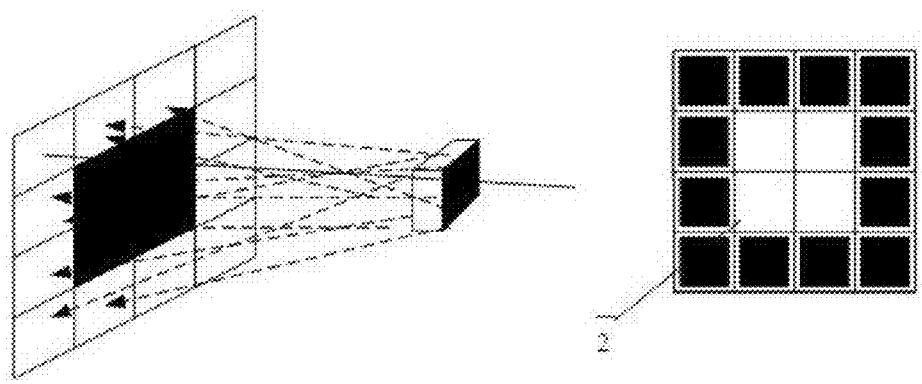
FIG. 34 is a schematic effect diagram of images collected by the radiation imaging system in Embodiment 3 of the present invention.

As shown in FIG. 33, the photon count detector in the traditional plane array collection mode, due to its inherent defects, will collect straight rays and scattered rays at the same time, making images collected by the photon count detector polluted, for example, shown by the area represented by reference sign 1 in FIG. 33. Images collected by the radiation imaging system provided in the present invention are as shown by the area represented by reference sign 2 in FIG. 34. It can be seen therefrom that, compared with the photon count detector in the traditional plane array collection mode, image collection achieved by the present invention significantly suppresses the scattered rays, and the image contrast and the signal-to-noise ratio are remarkably increased.

In actual use, it is difficult for the collection width to control the size of one pixel unit, and it is necessary to make a balance between the collection width and the contribution rate of the scattered rays. When a bettered de-scattering effect is required, in the case that the requirement for the collection speed is not high, it is feasible to choose a narrower X-ray beam as much as possible and simultaneously activate a smaller pixel unit area, and at this point, the pixel unit area may be one row of pixel units, multiple rows of pixel units, a pixel unit block formed by several adjacent pixel units, and at least, may even be one pixel unit; and vice versa. The order in which the pixel units are activated may be in a manner of first along the X direction and then along the Y direction, and may also be in other preset manners.

When images are collected point by point by taking a single pixel unit as an irradiation area, at this point, only one area (minimize to one pixel unit) is allowed to be in an activated state at each time, therefore, suppression capability for surrounding scattered rays is the strongest, the quality of the images collected is very high, but the collection speed is slow, which can be applied to occasions where the requirement for the collection speed is not very high. When line-by-line scanning is performed, as the line-by-line scanning mode is a state in which all pixel units in the line are activated simultaneously at the same time, there are still a small number of scattered rays collected by adjacent pixel units in the same line during line exposure and data collection. As the line-by-line scanning mode has a faster collection speed, in some situations where fast collection is required but the requirement for the image quality is not high, the line-by-line scanning mode is meaningful. In this way, the present invention can the demand for the image collection speed in different situations, thus obtaining images in line with actual demands, and even collect de-scattered images with higher precision.

For collection of multiple pixel units, it is feasible to increase one pre-processing module to solve the situation where the images are polluted. After each detector module preliminarily integrates the collected original data, the data is input to multiple photon count detector collection circuits, and then is sent to the pre-processing module via multiple data transmission channels. The pre-processing module may process, such as integrate, rearrange and correct, data frames, and the pre-processing module may also de-scatter and filter the data frames according to a de-scattering algorithm, to discriminate and discard related scattered data frames, but only retain effective data frames. The de-scattering algorithm of the pre-processing module may be implemented through FPGA, DSP and even an ASIC chip. The discriminated effective data frames are then sent to the host machine for concurrent image reconstruction. The de-scattering function of the scheme is implemented in the pre-processing module, there is no special requirement for the photon count detector, it is feasible to use the traditional photon count detector module, and it is unnecessary to redesign the photon count module.

In addition, according to the scheme, it is unnecessary to reconfigure the register during each scanning, and the scanning speed can be ensured, but the frame rate is not reduced. It is more flexible to implement the de-scattering function through FPGA, DSP and other programmable logic devices, different application demands and scanning modes can be implemented through hardware programming, to enable a set of detector systems to be compatible with multiple operation modes, greatly improving application flexibility of the detector systems. At the same time, the reconstructed original data received by the host machine is pre-processed, which reduces the data volume, simplifies complexity of the image reconstruction algorithm, and can reduce the requirement of the host machine for image reconstruction hardware resources.

This embodiment can adapt to detection requirements of different parts without increasing the radiation dose. At the same time, in the case of the same scanning time, the data processing volume is greatly reduced, the image effect is evidently increased, tiny details can be restored, and the requirement of medical diagnosis is fitted. During X-ray imaging in the case of reconstruction of two-dimensional images and three-dimensional images, by use of the method provided in the present invention, influences of scattered rays on images can be reduced, the image signal quality is enhanced, and the radiation dose can be reduced indirectly.

For a designed photon count detector hardware system, to keep integrity of the system, when the system is upgraded, it is feasible to adopt a scheme of software de-scattering.

The original data of the photon count detector unit goes through data pre-processing and frame data pre-processing sequentially, and then is sent to the host machine through a high-speed optical fiber transmission channel. After the host machine receives the frame data, a scattering and screening program is executed through a software algorithm, and the frame data, after scattering and screening, is image-reconstructed. The software algorithm is similar to the hardware algorithm of the pre-processing scheme, but is only achieved through different programming languages.

The biggest advantage to the scheme is that it is unnecessary to make any change to the hardware system and it is feasible to be compatible with the existing photon count detector system, which greatly reduces the hardware cost of the system. At the same time, the software de-scattering scheme has a shorter development cycle, and can get the product to the market faster. However, due to the absence of hardware-level pre-processing, data transmission pressure is increased. Meanwhile, higher requirements are proposed for hardware resources of the host machine.

The above describes the photon count-based radiation imaging system, method and devices thereof provided in the present invention in detail. Any obvious variation made by those of ordinary skill in the art without departing from the essence and the spirit of the present invention will infringe upon the patent right of the present invention, and may bear the corresponding legal responsibility.

What is claimed is:

1. A photon count-based radiation imaging system, comprising:
    an X-ray source, a scanning platform for bearing a sample, a photon count detector and a three-dimensional reconstruction system;
    wherein the X-ray source emits X-rays to the sample on the scanning platform, when the X-rays penetrate the sample, photons carrying material feature information in spatial positions are generated, and the photon count detector counts photons on an imaging plane, measures photon energy on each spatial position, obtains projection data and energy data of incident photons, and transmits the projection data and the energy data to the three-dimensional reconstruction system; wherein data of each pixel unit includes a counting sum and a cumulative sum of multiple energy levels, the counting sum indicates photon event energy information on the pixel unit, and the cumulative sum indicates density-related absorption attenuation information obtained by the pixel unit;
    the three-dimensional reconstruction system reconstructs three-dimensional structures and matter composition classes inside the sample according to the projection data and the energy data, and digitally dyes components of the sample, to identify matter composition of the sample.

2. A photon count-based radiation imaging method, implemented based on the radiation imaging system according to claim 1, comprising:
    (1) the X-ray source emitting X-rays to the sample on the scanning platform, and, when the X-rays penetrate the sample, generating photons carrying material feature information in spatial positions;
    (2) the photon count detector counting photons on an imaging plane, obtaining projection data and energy data of incident photons, and transmitting the photons to the three-dimensional reconstruction system; and
    (3) the three-dimensional reconstruction system reconstructing a three-dimensional structure and a matter composition class inside the sample according to the projection data and the energy data, and digitally dying components of the sample, to identify matter composition of the sample.

3. The radiation imaging method according to claim 2, wherein
    in step (1), photon accumulated values of points of each pixel unit obtained by the photon count detector through the counter form a projection map, and an energy distribution map is obtained through the level discrimination comparator; wherein the projection map is used for reconstructing the three-dimensional structure of the sample, and the energy distribution map is used for identifying the matter composition inside the sample.

4. The radiation imaging method according to claim 2, wherein
    in step (3), the digital dyeing is implemented based on different dimensions; in the process of digital dyeing, a two-dimensional projection map is collected and reconstructed with the different dimensions, and an arithmetical operation is performed on voxel parameters between reconstructed identical dimensions, to obtain a new dyeing parameter.

5. The radiation imaging method according to claim 1, wherein
    an anode target surface of the X-ray source is tungsten, and the filter is any one of aluminum, molybdenum, rhodium and beryllium.

6. The radiation imaging method according to claim 1, wherein
    a distance between the X-ray source and the sample is $R1=Ls*Fs/\lambda$;
    wherein Ls is a spatially coherent length, Fs is a focal point size, and $\lambda$ is an X-ray wavelength.

7. The radiation imaging method according to claim 1, wherein
    a distance between the sample and the photon count detector is $R2\approx\delta*\delta*M/\lambda$;
    wherein $\lambda$ is an X-ray wavelength, M is a magnification factor, $M=(R1+R2)/R1$, and $\delta$ is the detail to be identified by the sample.

8. The radiation imaging method according to claim 1, wherein
    the photon count detector is a plane-array detector made up of multiple pixel units, each pixel unit measures intensity of captured photons, and obtains intensity information on the position of the pixel unit by recording the total number of the photons captured in a particular time window; and each pixel unit compares the threshold of each captured X-photon,to measure energy level of the X-photon.

9. The radiation imaging method according to claim 2, wherein
    in step (1), the X-ray source emits the X-rays through bremsstrahlung, and after low-energy parts and high-energy parts of the X-rays are filtered through a filter, near monochromatic X rays are obtained.

* * * * *